(12) United States Patent
Bardiot et al.

(10) Patent No.: US 11,179,368 B2
(45) Date of Patent: Nov. 23, 2021

(54) SUBSTITUTED INDOLINE DERIVATIVES AS DENGUE VIRAL REPLICATION INHIBITORS

(71) Applicants: JANSSEN PHARMACEUTICALS, INC., Titusville, NJ (US); KATHOLIEKE UNIVERSITEIT LEUVEN, Leuven (BE)

(72) Inventors: Dorothée Alice Marie-Eve Bardiot, Leuven (BE); Bart Rudolf Romanie Kesteleyn, Beerse (BE); Jean-François Bonfanti, Issy-les-Moulineaux (FR); Pierre Jean-Marie Bernard Raboisson, Beerse (BE); Arnaud Didier M Marchand, Leuven (BE)

(73) Assignees: JANSSEN PHARMACEUTICALS, INC., Titusville, NJ (US); KATHOLIEKE UNIVERSITEIT LEUVEN, Leuven (BE)

( * ) Notice: Subject to any disclaimer, the term of this patent is extended or adjusted under 35 U.S.C. 154(b) by 15 days.

(21) Appl. No.: 16/492,667

(22) PCT Filed: Mar. 29, 2018

(86) PCT No.: PCT/EP2018/058077
§ 371 (c)(1),
(2) Date: Sep. 10, 2019

(87) PCT Pub. No.: WO2018/178238
PCT Pub. Date: Oct. 4, 2018

(65) Prior Publication Data
US 2020/0054606 A1    Feb. 20, 2020

(30) Foreign Application Priority Data

Mar. 31, 2017  (EP) ..................................... 17164045

(51) Int. Cl.
A61K 31/4045    (2006.01)
A61P 31/14       (2006.01)
C07D 209/32     (2006.01)

(52) U.S. Cl.
CPC .......... *A61K 31/4045* (2013.01); *A61P 31/14* (2018.01); *C07D 209/32* (2013.01)

(58) Field of Classification Search
CPC ............................ C07D 209/32; C07D 209/04; A61K 31/4045; A61K 45/06; A61P 31/14; A61P 31/12
See application file for complete search history.

(56) References Cited

U.S. PATENT DOCUMENTS 6,177,426 B1   1/2001   Denney et al.
7,601,735 B2   10/2009  Tyms et al.
8,143,259 B2   3/2012   Colburn et al.
8,299,056 B2   10/2012  Bahmanyar et al.
8,324,217 B2   12/2012  Colburn et al.
8,524,764 B2   9/2013   Canales et al.
8,884,030 B2   11/2014  Canales et al.
8,993,604 B2   3/2015   Byrd et al.
9,029,376 B2   5/2015   Byrd et al.
9,522,923 B2   12/2016  Richards et al.
9,944,598 B2   4/2018   Kesteleyn et al.
10,029,984 B2* 7/2018   Kesteleyn ............... A61P 43/00
10,064,870 B2  9/2018   Rajagopalan et al.
10,071,961 B2  9/2018   Vandyck et al.
10,117,850 B2  11/2018  Griffioen et al.
10,209,902 B1  2/2019   Kesteleyn et al.
10,323,026 B2  6/2019   Ikeda et al.
2005/0239821 A1  10/2005  Neyts et al.
2006/0194835 A1  8/2006   Dugourd et al.
2006/0211698 A1  9/2006   Botyanszki et al.
2008/0318338 A1  12/2008  Kamal et al.
2013/0023532 A1  1/2013   Casillas et al.
2014/0213586 A1  7/2014   Bardiot et al.
2016/0297810 A1  10/2016  Bardiot et al.
2017/0002006 A1  1/2017   Corte et al.
2017/0096429 A1  4/2017   Corte et al.
2017/0281633 A1  10/2017  Boylan et al.

(Continued)

FOREIGN PATENT DOCUMENTS

JP      2012-206959 A    10/2012
WO      99-21559 A1       5/1999

(Continued)

OTHER PUBLICATIONS

PCT International Search Report and Written Opinion dated Jun. 7, 2018 in connection with PCT International Application No. PCT/EP2018/058077.
Prasad L. Polavarapu, et al., Intrinsic Rotation and Molecular Structure, Chirality 15: S143-S149 (2003).
Prevention, Dengue, Centers for Disease Control and Prevention (Sep. 27, 2012) https://www.cdc.govidengue/prevention/index.html, internet.
Lidia Moreira Lima et al., Bioisosterism: A Useful Strategy for Molecular Modification and Drug Design, Current Medicinal Chemistry, Bentham Science Publishers Ltd. (2005) 12, pp. 23-49.

(Continued)

*Primary Examiner* — Amanda L. Aguirre
(74) *Attorney, Agent, or Firm* — Burns & Levinson, LLP; Shawn P. Foley

(57) ABSTRACT

The present invention concerns substituted indoline derivatives, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

10 Claims, No Drawings

Specification includes a Sequence Listing.

(56) References Cited

U.S. PATENT DOCUMENTS

| | | |
|---|---|---|
| 2017/0281766 A1 | 10/2017 | Wiltzius |
| 2017/0283500 A1 | 10/2017 | Wiltzius et al. |
| 2017/0298017 A1 | 10/2017 | Kesteleyn et al. |
| 2018/0346419 A1 | 12/2018 | Kesteleyn et al. |
| 2019/0104738 A1 | 4/2019 | Narine et al. |
| 2019/0112266 A1 | 4/2019 | Kesteleyn et al. |
| 2019/0183931 A1 | 6/2019 | Bakker et al. |

FOREIGN PATENT DOCUMENTS

| | | | |
|---|---|---|---|
| WO | 02089780 A2 | 11/2002 | |
| WO | 03050295 A2 | 6/2003 | |
| WO | 2006076529 A1 | 7/2006 | |
| WO | 2009149054 A1 | 12/2009 | |
| WO | 2010021878 A1 | 2/2010 | |
| WO | 2010027500 A1 | 3/2010 | |
| WO | 2010091413 A1 | 8/2010 | |
| WO | 2011037643 A2 | 3/2011 | |
| WO | 2011088303 A1 | 7/2011 | |
| WO | 2011-120025 A1 | 9/2011 | |
| WO | 2013045516 A1 | 4/2013 | |
| WO | WO-2013045516 A1 * | 4/2013 | ........... C07D 403/08 |
| WO | 2014154682 A1 | 10/2014 | |
| WO | 2016050831 A1 | 4/2016 | |
| WO | 2016050841 A1 | 4/2016 | |
| WO | 2016053455 A1 | 4/2016 | |
| WO | 2017046255 A1 | 3/2017 | |
| WO | 2017046258 A1 | 3/2017 | |
| WO | 2017079216 A1 | 5/2017 | |
| WO | 2017167832 A1 | 10/2017 | |
| WO | 2017167950 A1 | 10/2017 | |
| WO | 2017167951 A1 | 10/2017 | |
| WO | 2017167952 A1 | 10/2017 | |
| WO | 2017167953 A1 | 10/2017 | |
| WO | 2017171100 A1 | 10/2017 | |
| WO | 2017173206 A1 | 10/2017 | |
| WO | 2017173256 A1 | 10/2017 | |
| WO | 2017173384 A1 | 10/2017 | |
| WO | 2017173410 A1 | 10/2017 | |
| WO | 2018178240 A1 | 10/2018 | |
| WO | 2018215315 A1 | 11/2018 | |
| WO | 20188215316 A1 | 11/2018 | |

OTHER PUBLICATIONS

Ian Stansfield et al., Development of carboxylic acid replacements in indole-N-acetamide inhibitors of hepatitis C virus NS5B polymerase, Bioorganic & Medicinal Chemistry Letters 17 (2007) 5143-5149, ScienceDirect (2007), www.sciencedirect.com, internet.
Boltromeyuk V.V., Obshchaya khimiya (General Chemistry), Minsk, Vysheyshaya shkola, 2012, p. 65) (translation).
Wolff et al., Burger's Medicinal Chemistry and Drug Discovery, 5th Ed. part 1, p. 975-977 (1995).
Banker, et al., (1996) Modern Pharmaceuticals, 3rd Edition, Revised and Expanded, p. 596.
N.C.B.I.: "qHTS for inhibitors of binding or entry into cells for Marburg Virus," Pubchem Bioassay Record AID 540276, Jul. 2011, 13 pages, XP55641386, Retrieved from the Internet: https://pubchem.ncbi.nlm.nih.gov/bioassay/540276.
EP Search Report dated Nov. 19, 2019 from European Patent Appln. No. EP 19183201.3.
"Solvation," Wikipedia, at internet address: https://en.wikipedia.org/wiki/Solvation, web page last edited on Mar. 13, 2019, 6 pages.
Examination Report dated Jan. 7, 2020 from Indian Patent Appln. No. 201727014547.
Japanese Office Action dated Jun. 2, 2020 from Japanese Patent Appln. No. JP2017-243354 (English language translation).
ACS on STN Registry No. 931079-09-3, Apr. 20, 2007.
ACS on STN Registry No. 931007-71-5, Apr. 19, 2007.
ACS on STN Registry No. 930910-25-1, Apr. 19, 2007.
ACS on STN Registry No. 930724-99-5, Apr. 18, 2007.
ACS on STN Registry No. 930463-83-5, Apr. 17, 2007.
ACS on STN Registry No. 925399-60-6, Mar. 7, 2007.
ACS on STN Registry No. 920950-24-9, Feb. 14, 2007.
ACS on STN Registry No. 920926-40-5, Feb. 14, 2007.
ACS on STN Registry No. 920888-80-8, Feb. 14, 2007.
ACS on STN Registry No. 920870-55-9, Feb. 14, 2007.
ACS on STN Registry No. 920827-69-6, Feb. 14, 2007.
ACS on STN Registry No. 920696-97-5, Feb. 13, 2007.
ACS on STN Registry No. 920694-81-1, Feb. 13, 2007.
ACS on STN Registry No. 920668-38-8, Feb. 13, 2007.
ACS on STN Registry No. 879164-92-8, Apr. 4, 2006.
ACS on STN Registry No. 878462-38-5, Mar. 29, 2006.
ACS on STN Registry No. 853320-15-7, Jun. 30, 2005.

* cited by examiner

SEQUENCE LISTING

<160> NUMBER OF SEQ ID NOS: 6

<210> SEQ ID NO 1
<211> LENGTH: 19
<212> TYPE: DNA
<213> ORGANISM: Dengue virus group

<400> SEQUENCE: 1
cggttagagg agacccctc                                            19

<210> SEQ ID NO 2
<211> LENGTH: 21
<212> TYPE: DNA
<213> ORGANISM: Dengue virus group

<400> SEQUENCE: 2
gagacagcag gatctctggt c                                         21

<210> SEQ ID NO 3
<211> LENGTH: 28
<212> TYPE: DNA
<213> ORGANISM: Dengue virus group

<400> SEQUENCE: 3
aaggactaga ggttagagga gaccccc                                   28

<210> SEQ ID NO 4
<211> LENGTH: 18
<212> TYPE: DNA
<213> ORGANISM: Dengue virus group

<400> SEQUENCE: 4
ggccaggtca tcaccatt                                             18

<210> SEQ ID NO 5
<211> LENGTH: 21
<212> TYPE: DNA
<213> ORGANISM: Dengue virus group

<400> SEQUENCE: 5
atgtccacgt cacacttcat g                                         21

<210> SEQ ID NO 6
<211> LENGTH: 21

```
<212> TYPE: DNA
<213> ORGANISM: Dengue virus group

<400> SEQUENCE: 6
ttccgctgcc ctgaggctct c                                           21
```

SUBSTITUTED INDOLINE DERIVATIVES AS DENGUE VIRAL REPLICATION INHIBITORS

CROSS-REFERENCE TO RELATED APPLICATIONS

This application is a U.S. national stage entry under 35 U.S.C. § 371 of PCT International Patent Application No. PCT/EP2018/058077, filed Mar. 29, 2018, which claims priority to European Patent Application No. 17164045.1, filed Mar. 31, 2017.

The present invention relates to substituted indoline derivatives, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known, so-called DENV-1, -2, -3, and -4. Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

Although progress is being made in the development of vaccines against dengue with the availability of the Dengvaxia® vaccine, many difficulties are encountered. These include the existence of a phenomenon referred to as antibody-dependent enhancement (ADE). Recovery from an infection by one serotype provides lifelong immunity against that serotype but confers only partial and transient protection against a subsequent infection by one of the other three serotypes.

Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titers. In both primary and secondary infections, higher viral titers are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyper endemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

The mosquitoes that carry dengue, including *Aedes aegypti* and *Aedes albopictus* (tiger mosquito), are moving north on the globe. According to the United States (US) Centers for Disease Control and Prevention (CDC), both mosquitoes are currently omnipresent in southern Texas. The spread north of dengue-carrying mosquitoes is not confined to the US, but has also been observed in Europe.

Dengvaxia®, the dengue vaccine produced by Sanofi Pasteur was first approved in Mexico and has received in the meantime approval in more countries. Nevertheless, the vaccine leaves considerable room for improvement due to limited efficacy, especially against DENV-1 and -2, low efficacy in flavivirus-naïve subjects and the lengthy dosing schedule.

Despite these shortcomings, the vaccine is a game changer in endemic settings as it will offer protection to a large part of the population, but likely not to very young infants, who bear the largest burden of dengue. In addition, the dosing schedule and very limited efficacy in flavivirus-naïve subjects make it unsuitable and likely not worthwhile/cost-effective for travelers from non-endemic areas to dengue-endemic areas. The above mentioned shortcomings of the dengue vaccines are the reason why there is a need for a pre-exposure prophylactic dengue antiviral.

Furthermore, today, specific antiviral drugs for the treatment or prevention of dengue fever virus infection are not available. Clearly, there is still a great unmet medical need for therapeutics for the prevention or treatment of viral infections in animals, more in particular in humans and especially for viral infections caused by flaviviruses, more in particular Dengue virus. Compounds with good anti-viral potency, no or low levels of side-effects, a broad spectrum activity against multiple Dengue virus serotypes, a low toxicity and/or good pharmacokinetic or -dynamic properties are highly needed.

WO-2010/021878 discloses 2-phenylpyrrolidine and indoline derivatives as cold menthol receptor antagonists for treatment of inflammatory and central diseases. WO-2013/045516 discloses indole and indoline derivatives for use in the treatment of dengue viral infections.

The present invention now provides compounds, substituted indoline derivatives, which show high potent activity against all four (4) serotypes of the Dengue virus.

SUMMARY OF THE INVENTION

The present invention is based on the unexpected finding that at least one of the above-mentioned problems can be solved by the current compounds of the invention.

The present invention provides compounds which have been shown to possess potent antiviral activity against all four (4) serotypes currently known. The present invention furthermore demonstrates that these compounds efficiently inhibit proliferation of Dengue virus (DENV). Therefore, these compounds constitute a useful class of potent compounds that can be used in the treatment and/or prevention of viral infections in animals, mammals and humans, more specifically for the treatment and/or prevention of infections with Dengue viruses.

The present invention furthermore relates to the use of such compounds as medicines and to their use for the manufacture of medicaments for treating and/or preventing viral infections, in particular with viruses belonging to the family of the Dengue viruses in animals or mammals, more in particular in humans. The invention also relates to methods for the preparation of all such compounds and to pharmaceutical compositions comprising them in an effective amount.

The present invention also relates to a method of treatment or prevention of dengue viral infections in humans by the administration an effective amount of one or more such compounds, or a pharmaceutically acceptable salt thereof optionally in combination with one or more other medicines, like another antiviral agent, to a patient in need thereof.

One aspect of the invention is the provision compounds of formula (I), including any stereochemically isomeric form thereof:

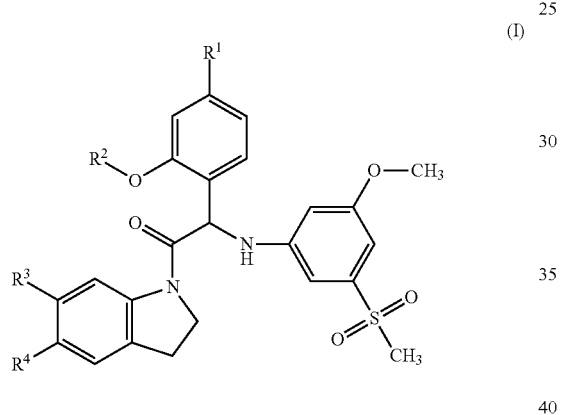

(I)

wherein $R^1$ is fluoro, $R^2$ is —$CH_2CH_2OH$, $R^3$ is trifluoromethyl, and $R^4$ is hydrogen, or $R^1$ is fluoro, $R^2$ is —$CH_2CH_2OH$, $R^3$ is trifluoromethyl, and $R^4$ is methoxy, or $R^1$ is fluoro, $R^2$ is —$CH_2CH_2OH$, $R^3$ is trifluoromethoxy, and $R^4$ is hydrogen, or $R^1$ is chloro, $R^2$ is —$CH_2CH_2OH$, $R^3$ is trifluoromethyl, and $R^4$ is hydrogen, or $R^1$ is chloro, $R^2$ is —$CH_2CH_2OH$, $R^3$ is trifluoromethyl, and $R^4$ is methoxy, or $R^1$ is chloro, $R^2$ is —$CH_2CH_2OH$, $R^3$ is trifluoromethoxy, and $R^4$ is hydrogen, or $R^1$ is chloro, $R^2$ is —$(CH_2)_3COOH$, $R^3$ is trifluoromethyl, and $R^4$ is hydrogen, or $R^1$ is chloro, $R^2$ is —$(CH_2)_3COOH$, $R^3$ is trifluoromethyl, and $R^4$ is methoxy, or $R^1$ is chloro, $R^2$ is —$(CH_2)_3COOH$, $R^3$ is trifluoromethoxy, and $R^4$ is hydrogen;

or a pharmaceutically acceptable salt, solvate or polymorph thereof.

Specifically above mentioned compounds are selected from the group comprising:

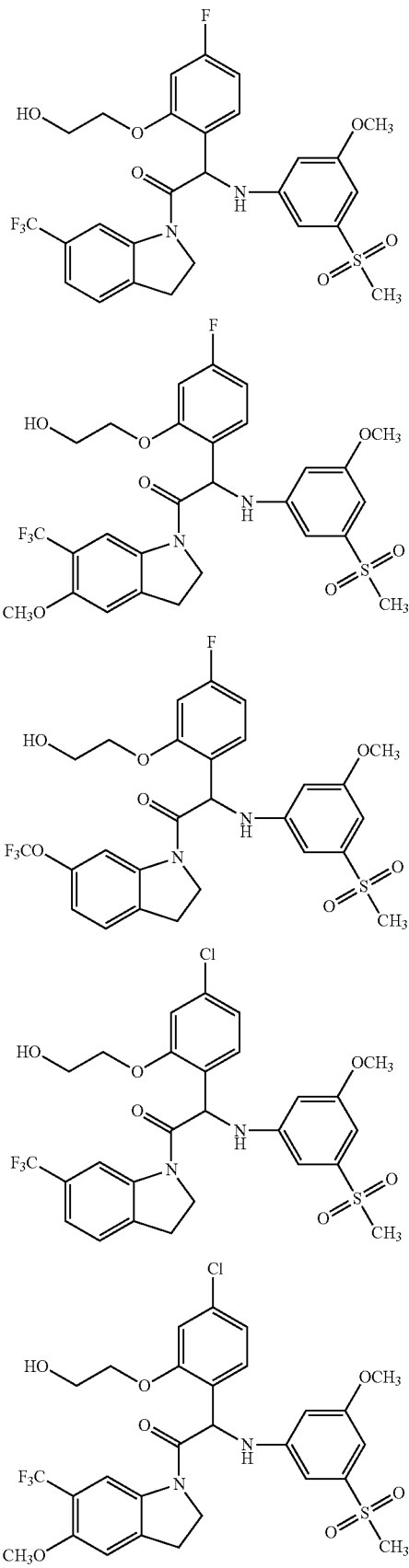

-continued

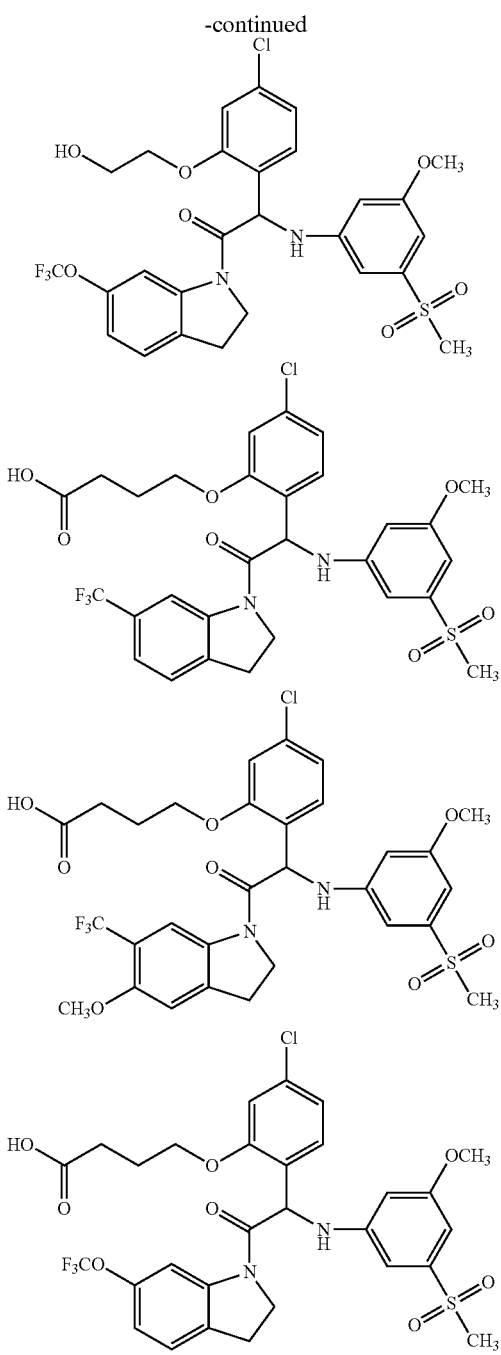

Part of the current invention is also a pharmaceutical composition comprising a compound mentioned above or a stereoisomeric form, a pharmaceutically acceptable salt, solvate or polymorph thereof together with one or more pharmaceutically acceptable excipients, diluents or carriers.

Pharmaceutically acceptable salts of said compounds include the acid addition and base salts thereof. Suitable acid addition salts are formed from acids which form non-toxic salts. Suitable base salts are formed from bases which form non-toxic salts.

The pharmaceutically acceptable acid salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-amino-salicylic, pamoic acid and the like acids.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral or rectal administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of the invention used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14.

The present compounds used in the current invention may also exist in their stereochemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereochemically isomeric forms, which said compounds might possess.

Said mixture may contain all diastereomers and/or enantiomers of the basic molecular structure of said compound. All stereochemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The compounds of formula (I) of the present invention all have at least one chiral carbon atom as indicated in the figure below by the carbon atom labelled with *:

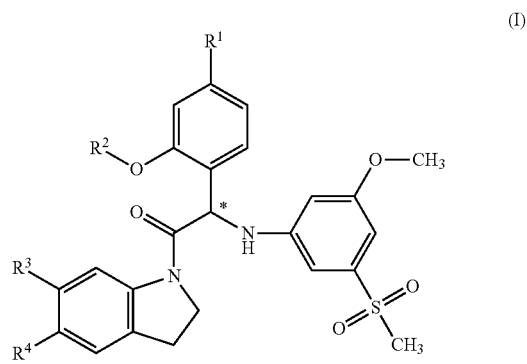

Due to the presence of said chiral carbon atom, a "compound of formula (I)" can be the (R)-enantiomer, the (S)-enantiomer, the racemic form, or any possible combination of the two individual enantiomers in any ratio. When the absolute (R)- or (S)-configuration of an enantiomer is not known, this enantiomer can also be identified by indicating whether the enantiomer is dextrorotatory (+)- or levorotatory (−)-after measuring the specific optical rotation of said particular enantiomer.

In an aspect the present invention relates to a first group of compound of formula (I) wherein the compounds of formula (I) have the (+) specific rotation.

In a further aspect the present invention relates to a second ground of compounds of formula (I) wherein the compounds of formula (I) have the (−) specific rotation.

EXAMPLES

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the [M+H]$^+$ (protonated molecule) and/or [M−H]$^−$ (deprotonated molecule). In case the compound was not directly ionizable the type of adduct is specified (i.e. [M+NH$_4$]$^+$, [M+HCOO]$^−$, etc. . . . ). For molecules with multiple isotopic patterns (Br, CI), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

LC/MS Method codes (Flow expressed in mL/min; column temperature (T) in ° C.; Run time in minutes).

| Method code | Instrument | Column | Mobile phase | Gradient | Flow Col T | Run time (min) |
|---|---|---|---|---|---|---|
| LC-A | Waters: Acquity ® UPLC ®-DAD-Quattro Micro ™ | Waters: BEH ® C18 (1.7 µm, 2.1 × 100 mm) | A: 95% CH$_3$COONH$_4$ 7 mM/5% CH$_3$CN, B: CH$_3$CN | 84.2% A for 0.49 min, to 10.5% A in 2.18 min, held for 1.94 min, back to 84.2% A in 0.73 min, held for 0.73 min. | 0.343 mL/min 40° C. | 6.2 |
| LC-B | Waters: Acquity ® H-Class-DAD and SQD2TM | Waters: BEH ® C18 (1.7 µm, 2.1 × 100 mm) | A: 95% CH$_3$COONH$_4$ 7 mM/5% CH$_3$CN, B: CH$_3$CN | 84.2% A/15.8% B to 10.5% A in 2.18 min, held for 1.96 min, back to 84.2% A/15.8% B in 0.73 min, held for 0.49 min. | 0.343 mL/min 40° C. | 6.1 |
| LC-C | Waters: Acquity ® UPLC ®-DAD-Acquity ® TQ detector | Waters: UPLC HSS C18 (1.8 µm, 2.1 × 50 mm) | A: 0.1% HCOOH B: CH$_3$CN | 50% A to 10% A in 3.5 min, held for 1.5 min. | 0.5 mL/min 40° C. | 5 |
| LC-D | Waters: Acquity ® UPLC ®-DAD-SQD | Waters: BEH C18 (1.7 µm, 2.1 × 50 mm) | A: 10 mM CH$_3$COONH$_4$ in 95% H$_2$O + 5% CH$_3$CN B: CH$_3$CN | From 95% A to 5% A in 1.3 min, held for 0.7 min. | 0.8 mL/min 55° C. | 2 |

SFC/MS Methods

The SFC measurement was performed using an Analytical Supercritical fluid chromatography (SFC) system composed by a binary pump for delivering carbon dioxide (CO$_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Analytical SFC/MS Methods (Flow expressed in mL/min; column temperature (T) in ° C.; Run time in minutes, Backpressure (BPR) in bars.

| Method code | column | mobile phase | gradient | Flow Col T | Run time BPR |
|---|---|---|---|---|---|
| SFC-A | Daicel Chiralpak ® AD-H column (5 µm, 150 × 4.6 mm) | A: CO$_2$ B: EtOH (+0.3% iPrNH$_2$) | 20% B hold 7 min, | 3 35 | 7 100 |
| SFC-B | Regis Whelk O1 ®(S,S) column (3 µm, 100 × 4.6 mm) | A: CO$_2$ B: EtOH (+0.3% iPrNH$_2$) | 50% B hold 3 min, | 3.5 35 | 3 103 |
| SFC-C | Daicel Chiralpak ® AD-H column (5 µm, 150 × 4.6 mm) | A: CO$_2$ B: EtOH (+0.3% iPrNH$_2$) | 30% B hold 7 min, | 3 35 | 7 100 |
| SFC-D | Daicel Chiralpak ® IC-3 column (3 µm, 100 × 4.6 mm) | A: CO$_2$ B: EtOH (+0.3% iPrNH$_2$) | 40% B hold 3 min, | 3.5 35 | 3 103 |
| SFC-E | Daicel Chiralpak ® IA column (5 µm, 150 × | A: CO$_2$ B: iPrOH (+0.3% | 30% B hold 7 min, | 3.5 | 7 |

-continued

| Method code | column | mobile phase | gradient | Flow Col T | Run time BPR |
|---|---|---|---|---|---|
| | 4.6 mm) | iPrNH$_2$) | | 35 | 103 |
| SFC-F | Daicel Chiralpak ® IC column (5 µm, 150 × 4.6 mm) | A: CO$_2$ B: MeOH | 30% B hold 7 min, | 3 35 | 7 100 |
| SFC-G | Daicel Chiralpak ® IC-3 column (3 µm, 100 × 4.6 mm) | A: CO$_2$ B: iPrOH (+0.3% iPrNH$_2$) | 40% B hold 5 min, | 3.5 35 | 5 103 |
| SFC-H | Daicel Chiralpak ® IC column (5 µm, 150 × 4.6 mm) | A: CO$_2$ B: EtOH/iPrOH 50/50 (+0.3% iPrNH$_2$) | 25% B hold 7 min, | 3 35 | 7 100 |
| SFC-I | Daicel Chiralpak ® AS3 column (3.0 µm, 150 × 4.6 mm) | A: CO$_2$ B: EtOH (+0.2% iPrNH$_2$ +3% H$_2$O) | 10%-50% B in 6 min, hold 3.5 min | 2.5 40 | 9.5 110 |

Melting Points

Values are either peak values or melt ranges, and are obtained with experimental uncertainties that are commonly associated with this analytical method.

DSC823e (Indicated as DSC)

For a number of compounds, melting points were determined with a DSC823e (Mettler-Toledo). Melting points were measured with a temperature gradient of 10° C./minute. Maximum temperature was 300° C.

Optical Rotations:

Optical rotations were measured on a Perkin-Elmer 341 polarimeter with a sodium lamp and reported as follows: $[\alpha]^\circ$ ($\lambda$, c g/100 ml, solvent, T° C.).

$[\alpha]_\lambda^T = (100\alpha)/(l \times c)$: where l is the path length in dm and c is the concentration in g/100 ml for a sample at a temperature T (° C.) and a wavelength $\lambda$ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

Abbreviations Used in Experimental Part

| | | |
|---|---|---|
| (M + H)$^+$ | protonated molecular ion | |
| aq. | aqueous | |
| Boc | tert-butyloxycarbonyl | |
| Boc$_2$O | di-tert-butyl dicarbonate | |
| br | broad | |
| CH$_3$CN | acetonitrile | |
| CHCl$_3$ | chloroform | |
| CH$_2$Cl$_2$ | dichloromethane | |
| CH$_3$OH | methanol | |
| CO$_2$ | carbon dioxide | |
| d | doublet | |
| DCM | dichloromethane | |
| DIEA | diisopropylethylamine | |
| DIPE | diisopropyl ether | |
| DMA | dimethylacetamide | |
| DMAP | 4-dimethylaminopyridine | |
| DME | 1,2-dimethoxyethane | |
| DMF | dimethylformamide | |
| DMSO | dimethyl sulfoxide | |
| eq. | equivalent | |
| Et$_2$O | diethyl ether | |
| Et$_3$N | triethylamine | |
| EtOAc | ethyl acetate | |
| EtOH | ethanol | |
| H$_2$O | water | |

-continued

| | |
|---|---|
| H$_2$SO$_4$ | sulfuric acid |
| HATU | O-(7-aza-1H-benzotriazol-1-yl)-N,N,N',N'-tetramethyl-uronium hexafluorophosphate-CAS [148893-10-1] |
| HCl | hydrochloric acid |
| HPLC | high performance liquid chromatography |
| iPrNH$_2$ | isopropylamine |
| iPrOH | 2-propanol |
| K$_2$CO$_3$ | potassium carbonate |
| LiAlH$_4$ | lithium aluminium hydride |
| m/z | mass-to-charge ratio |
| Me | methyl |
| MeOH | methanol |
| MgSO$_4$ | magnesium sulfate |
| min | minute(s) |
| N$_2$ | nitrogen |
| Na$_2$CO$_3$ | sodium carbonate |
| Na$_2$SO$_4$ | sodium sulfate |
| NaBH$_4$ | sodium borohydride |
| NaHCO$_3$ | sodium bicarbonate |
| NaOH | sodium hydroxide |
| NH$_4$Cl | ammonium chloride |
| q | quartet |
| rt or RT | room temperature |
| s | singlet |
| t | triplet |
| tBuOK | potassium tert-butanolaat |
| TEA | triethylamine |
| TFA | trifluoroacetic acid |
| THF | tetrahydrofuran |
| TMSCl | trimethylsilyl chloride |

Example 1: Synthesis of 2-(4-fluoro-2-(2-hydroxy-ethoxy)phenyl)-2-((3-methoxy-5-(methylsulfonyl)phenyl)amino)-1-(6-(trifluoromethyl)indolin-1-yl)ethan-1-one (Compound 1) and Chiral Separation into Enantiomers 1A and 1B

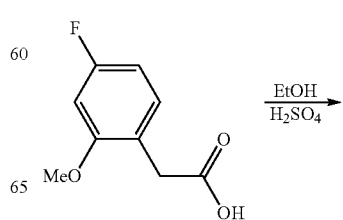

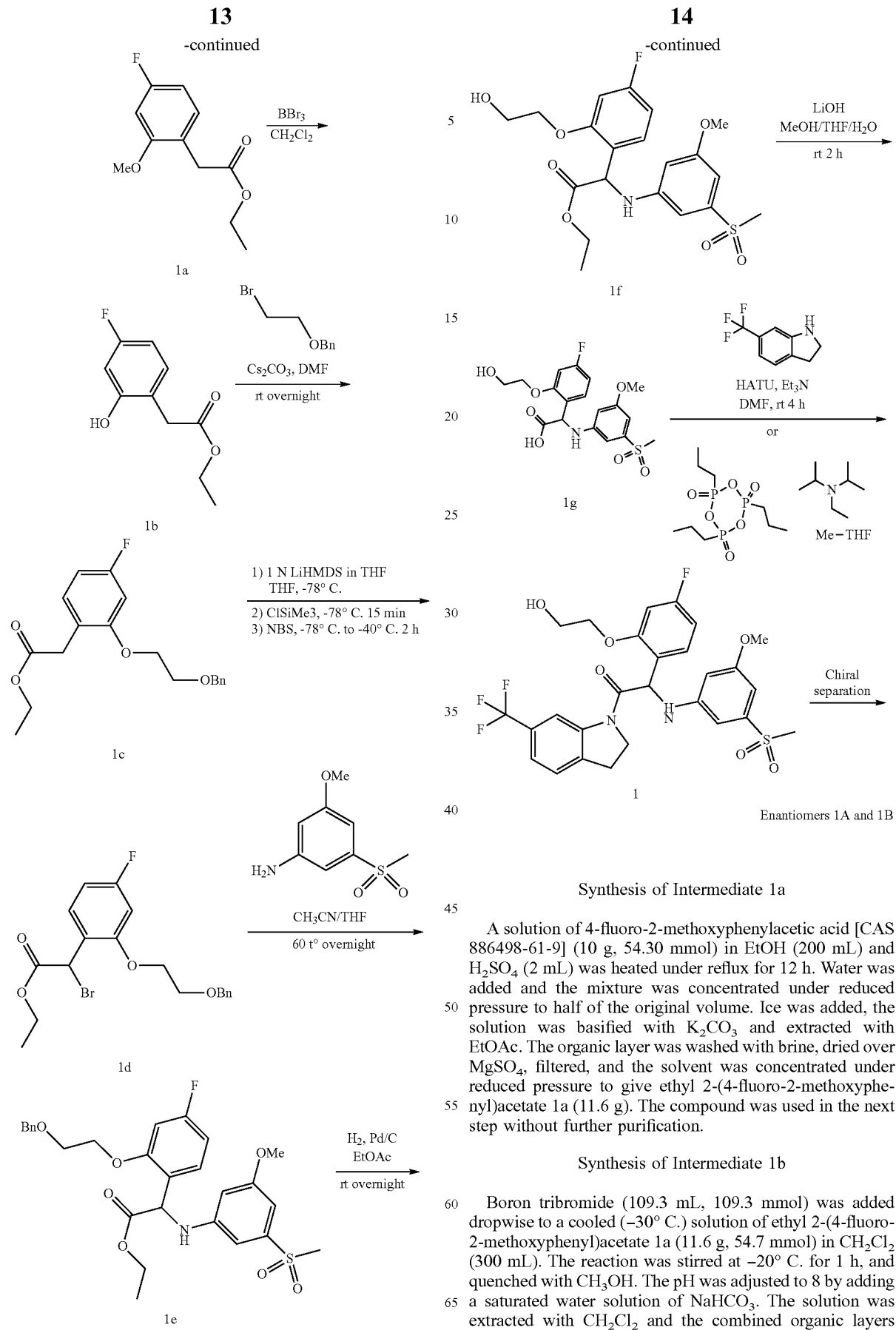

Synthesis of Intermediate 1a

A solution of 4-fluoro-2-methoxyphenylacetic acid [CAS 886498-61-9] (10 g, 54.30 mmol) in EtOH (200 mL) and $H_2SO_4$ (2 mL) was heated under reflux for 12 h. Water was added and the mixture was concentrated under reduced pressure to half of the original volume. Ice was added, the solution was basified with $K_2CO_3$ and extracted with EtOAc. The organic layer was washed with brine, dried over $MgSO_4$, filtered, and the solvent was concentrated under reduced pressure to give ethyl 2-(4-fluoro-2-methoxyphenyl)acetate 1a (11.6 g). The compound was used in the next step without further purification.

Synthesis of Intermediate 1b

Boron tribromide (109.3 mL, 109.3 mmol) was added dropwise to a cooled (−30° C.) solution of ethyl 2-(4-fluoro-2-methoxyphenyl)acetate 1a (11.6 g, 54.7 mmol) in $CH_2Cl_2$ (300 mL). The reaction was stirred at −20° C. for 1 h, and quenched with $CH_3OH$. The pH was adjusted to 8 by adding a saturated water solution of $NaHCO_3$. The solution was extracted with $CH_2Cl_2$ and the combined organic layers were dried over $MgSO_4$, filtered, and the solvent was concentrated under reduced pressure to give ethyl 2-(4-fluoro-2-hydroxyphenyl)acetate 1b (10.8 g). The compound was used in the next step without further purification.

Synthesis of Intermediate 1c

To a mixture of ethyl 2-(4-fluoro-2-hydroxyphenyl)acetate 1b (1.24 g, 6.26 mmol) and cesium carbonate (4.08 g, 12.5 mmol) in DMF (20 mL) was added benzyl 2-bromoethyl ether [CAS 1462-37-9] (1.61 g, 7.51 mmol). The reaction mixture was stirred at room temperature overnight. Water was added and the reaction mixture was extracted with EtOAc. The organic phase was dried over $Na_2SO_4$, filtered and concentrated under reduced pressure. The residue was purified by flash chromatography on silica gel using a gradient of $CH_2Cl_2$ (15% to 100%) in heptane to give ethyl 2-(2-(2-(benzyloxy)ethoxy)-4-fluorophenyl)acetate 1c (1.55 g).

Synthesis of Intermediate 1d

To a cooled (−78° C.) solution of 1M lithium bis(trimethylsilyl)amide in THF (4.51 mL, 4.51 mmol) was added a solution of ethyl 2-(2-(2-(benzyloxy)ethoxy)-4-fluorophenyl)acetate 1c (0.750 g, 2.26 mmol) in THF (4 mL). After 1 h at −78° C., chlorotrimethylsilane (0.458 mL, 3.61 mmol) was added. The reaction mixture was stirred at −78° C. for 15 min. N-Bromosuccinimide (0.482 g, 2.71 mmol) was added and stirring was continued at −40° C. for 2 h. The reaction mixture was poured out into $H_2O$ and extracted twice with EtOAc. The organic phases were combined, dried over $Na_2SO_4$, filtered and concentrated under reduced pressure to give ethyl 2-(2-(2-(benzyloxy)ethoxy)-4-fluorophenyl)-2-bromoacetate 1d (0.920 g) which was used in the next step without further purification.

Synthesis of Intermediate 1e

A mixture of ethyl 2-(2-(2-(benzyloxy)ethoxy)-4-fluorophenyl)-2-bromoacetate d (0.920 g, 2.24 mmol) and 3-methoxy-5-(methylsulfonyl)aniline [CAS 62606-02-4] (1.35 g, 6.71 mmol) in $CH_3CN$ (5 mL) and THF (5 mL) was stirred at 60° C. overnight. The reaction mixture was diluted with EtOAc and washed with 1N HCl. The organic phase was washed with 1N HCl, an aqueous saturated $NaHCO_3$ solution, $H_2O$ and brine, dried over $Na_2SO_4$, filtered and concentrated under reduced pressure. The residue was purified by flash chromatography on silica gel using a gradient of EtOAc (5% to 50%) in heptane to give ethyl 2-(2-(2-(benzyloxy)ethoxy)-4-fluorophenyl)-2-((3-methoxy-5-(methylsulfonyl) phenyl)amino)acetate 1e (0.870 g).

Synthesis of Intermediate 1f

A mixture of ethyl 2-(2-(2-(benzyloxy)ethoxy)-4-fluorophenyl)-2-((3-methoxy-5-(methylsulfonyl)phenyl)amino) acetate 1e (0.868 g, 1.63 mmol) and 10% palladium on carbon (0.180 g) in EtOAc (30 mL) was stirred overnight at room temperature under $H_2$ atmosphere. The reaction mixture was filtered through Celite®. The filtrate was concentrated under reduced pressure. The residue was purified by flash chromatography on silica gel using a gradient of EtOAc (30% to 100%) in heptane to give quantitatively ethyl 2-(4-fluoro-2-(2-hydroxyethoxy)phenyl)-2-((3-methoxy-5-(methylsulfonyl)phenyl)amino)acetate 1f.

Synthesis of Intermediate 1g

To a solution of ethyl 2-(4-fluoro-2-(2-hydroxyethoxy) phenyl)-2-((3-methoxy-5-(methylsulfonyl)phenyl)amino) acetate 1f (0.910 g, 2.06 mmol) in THF (6 mL), MeOH (6 mL) and $H_2O$ (6 mL) was added lithium hydroxide monohydrate (0.432 g, 10.3 mmol). The reaction mixture was stirred at room temperature for 2 h. The reaction mixture was partially concentrated under reduced pressure to remove THF and MeOH. The residual aqueous solution was acidified with 1N HCl and extracted with $CH_2Cl_2$. The organic phase was dried over $Na_2SO_4$, filtered and concentrated under reduced pressure to give 2-(4-fluoro-2-(2-hydroxyethoxy)phenyl)-2-((3-methoxy-5-(methylsulfonyl)phenyl) amino)acetic acid 1g (0.736 g) which was used in the next step without further purification.

Synthesis of Compound 1 and Chiral Separation into Enantiomers 1A and 1B

Method 1:
To a solution of 2-(4-fluoro-2-(2-hydroxyethoxy)phenyl)-2-((3-methoxy-5-(methylsulfonyl)phenyl)amino)acetic acid 1g (0.200 g, 0.484 mmol) in DMF (4 mL) were added HATU (0.184 g, 0.484 mmol), triethylamine (0.267 mL, 1.94 mmol) and 6-(trifluoromethyl)indoline [CAS 181513-29-1] (0.091 g, 0.484 mmol). The reaction mixture was stirred at room temperature for 4 h. The reaction mixture was diluted with EtOAc and washed with 1N HCl. The organic phase was washed with an aqueous saturated $NaHCO_3$ solution, $H_2O$ and brine, dried over $Na_2SO_4$, filtered and concentrated under reduced pressure. The residue was purified by flash chromatography on silica gel using a gradient of EtOAc (2% to 40%) in $CH_2Cl_2$. The fractions containing the desired product were combined and concentrated under reduced pressure. The residue was purified by preparative TLC using a mixture of EtOAc (50%) in $CH_2Cl_2$ as eluent. Subsequent purification by preparative HPLC (Column: X-Bridge® C18—5 μm 100×19 mm, mobile phase: pH 10 $NH_4OAc$ solution in $H_2O$, $CH_3CN$) furnished 2-(4-fluoro-2-(2-hydroxyethoxy)phenyl)-2-((3-methoxy-5-(methylsulfonyl) phenyl)amino)-1-(6-(trifluoromethyl)indolin-1-yl)ethanone (Compound 1, 0.043 g) as a racemic mixture.

Method 2:
To a solution of 2-(4-fluoro-2-(2-hydroxyethoxy)phenyl)-2-((3-methoxy-5-(methylsulfonyl)phenyl)amino)acetic acid 1g (0.300 g, 0.726 mmol) in Me-THF (5.4 mL) under $N_2$ flow, were added 6-(trifluoromethyl)indoline [CAS 181513-29-1](0.136 g, 0.726 mmol), N-diisopropylethylamine (264 μL, 1.596 mmol) and propylphosphonic anhydride (653 μL, 1.09 mmol). The reaction was stirred at room temperature for 16 h. The mixture was poured out into water and extracted with EtOAc. The combined organic layers were washed with a 10% solution of $K_2CO_3$ in water and with water. The organic solution was dried over $MgSO_4$, filtered and the solvent was concentrated under reduced pressure. This fraction (0.47 g) was combined with a second batch (total amount: 0.585 g) and purified by flash chromatography on silica gel (15-40 μM, 24 g, $CH_2Cl_2$/MeOH 99.5/0.5). The pure fractions were combined and concentrated under reduced pressure to provide 2-(4-fluoro-2-(2-hydroxyethoxy)phenyl)-2-((3-methoxy-5-(methylsulfonyl)phenyl) amino)-1-(6-(trifluoromethyl)indolin-1-yl)ethanone (Compound 1, 0.160 g) as a racemic mixture.

The Enantiomers of Compound 1 (160 mg) were separated via Preparative Chiral SFC (Stationary phase: Chiralpak® AD-H 5 μm 250×20 mm, Mobile phase: 75% $CO_2$, 25% EtOH (+0.3% $iPrNH_2$)). The first eluted product (72 mg) was solidified in heptane/diisopropyl ether to give Enantiomer 1A (50 mg). The second eluted product (80 mg) was solidified in heptane/diisopropyl ether to give Enantiomer 1B (43 mg).

Compound 1:

$^1$H NMR (300 MHz, DMSO-$d_6$) δ ppm 3.10 (s, 3H) 3.22 (m, 2H) 3.62-3.92 (m, 5H) 3.97-4.22 (m, 3H) 4.46 (m, 1H) 4.98 (br. s., 1H) 5.82 (d, J=7.9 Hz, 1H) 6.56 (s, 1H) 6.62 (s, 1H) 6.80 (t, J=7.7 Hz, 1H) 6.92 (s, 1H) 6.95-7.11 (m, 2H) 7.29-7.53 (m, 3H) 8.39 (s, 1H)

LC-MS (method LC-C): $R_t$ 1.37 min, MH$^+$ 583

Enantiomer 1A:

$^1$H NMR (500 MHz, DMSO-$d_6$) δ ppm 3.10 (s, 3H) 3.14-3.29 (m, 2H) 3.73 (s, 3H) 3.75-3.78 (m, 1H) 3.78-3.89 (m, 1H) 3.98-4.23 (m, 3H) 4.37-4.55 (m, 1H) 4.97 (t, J=5.4 Hz, 1H) 5.82 (d, J=8.2 Hz, 1H) 6.56 (s, 1H) 6.62 (s, 1H) 6.79 (dt, J=2.2, 8.5 Hz, 1H) 6.91 (s, 1H) 6.98-7.04 (m, 2H) 7.32-7.43 (m, 2H) 7.46 (d, J=7.9 Hz, 1H) 8.39 (s, 1H).

LC/MS (method LC-A): $R_t$ 3.04 min, MH$^+$ 583

$[\alpha]_D^{20}$: −49.6° (c 0.25, DMF)

Chiral SFC (method SFC-A): $R_t$ 2.76 min, MH$^+$ 583, chiral purity 100%.

Enantiomer 1B:

$^1$H NMR (500 MHz, DMSO-$d_6$) δ ppm 3.10 (s, 3H) 3.14-3.29 (m, 2H) 3.73 (s, 3H) 3.75-3.78 (m, 1H) 3.78-3.89 (m, 1H) 3.98-4.23 (m, 3H) 4.37-4.55 (m, 1H) 4.97 (t, J=5.4 Hz, 1H) 5.82 (d, J=8.2 Hz, 1H) 6.56 (s, 1H) 6.62 (s, 1H) 6.79 (dt, J=2.2, 8.5 Hz, 1H) 6.91 (s, 1H) 6.98-7.04 (m, 2H) 7.32-7.43 (m, 2H) 7.46 (d, J=7.9 Hz, 1H) 8.39 (s, 1H).

LC/MS (method LC-A): $R_t$ 3.04 min, MH$^+$ 583

$[\alpha]_D^{20}$: +51.7° (c 0.23, DMF)

Chiral SFC (method SFC-A): $R_t$ 4.16 min, MH$^+$ 583, chiral purity 100%.

Example 2: Synthesis of 2-(4-fluoro-2-(2-hydroxyethoxy)phenyl)-2-((3-methoxy-5-(methylsulfonyl)phenyl)amino)-1-(5-methoxy-6-(trifluoromethyl)indolin-1-yl)ethanone (Compound 2) and Chiral Separation into Enantiomers 2A and 2B

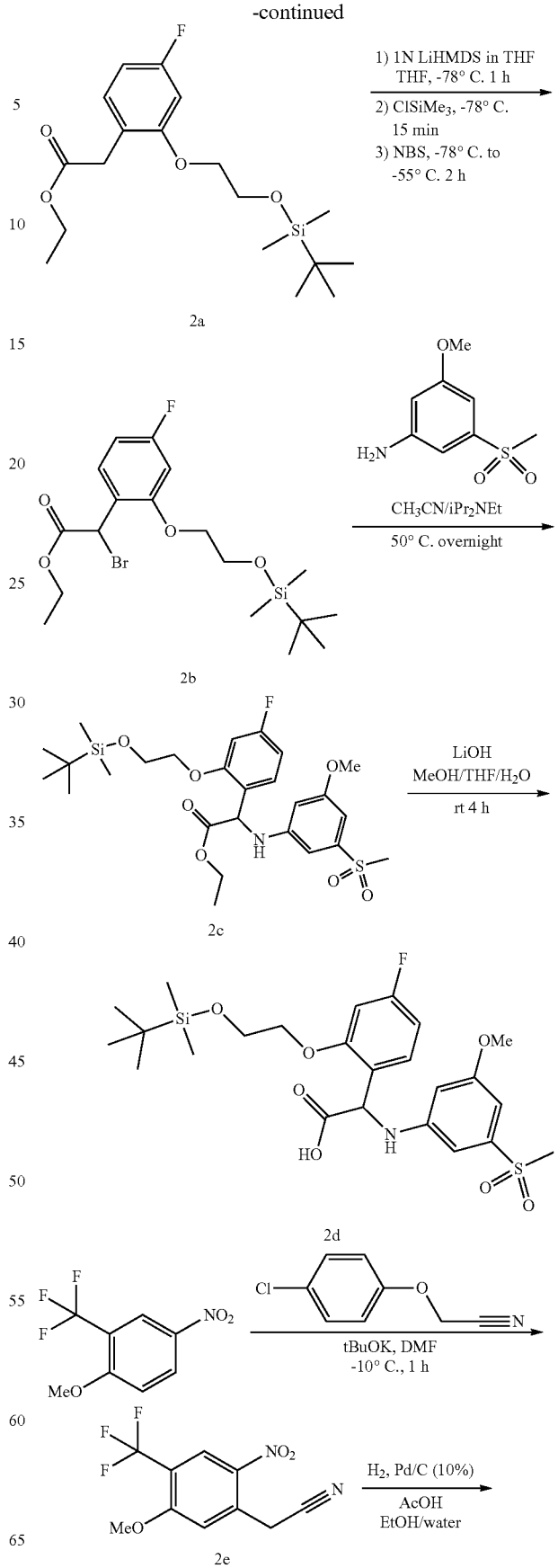

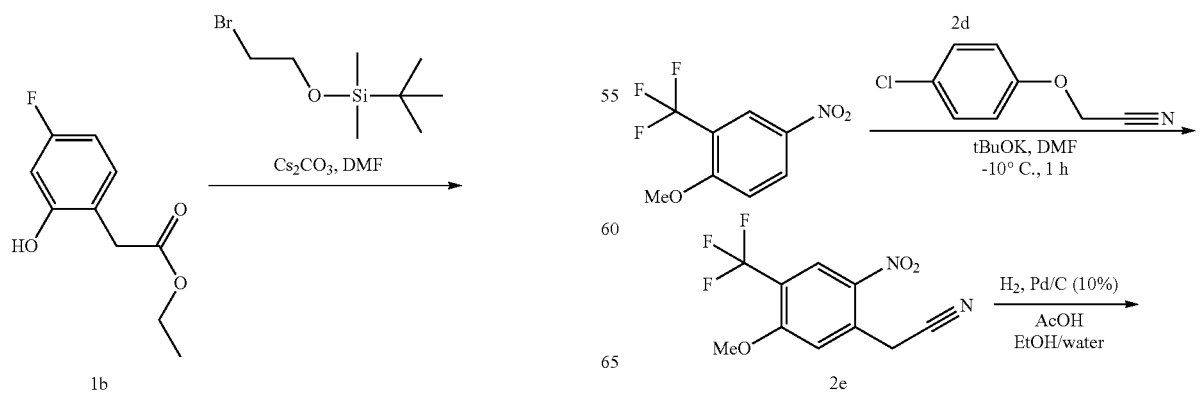

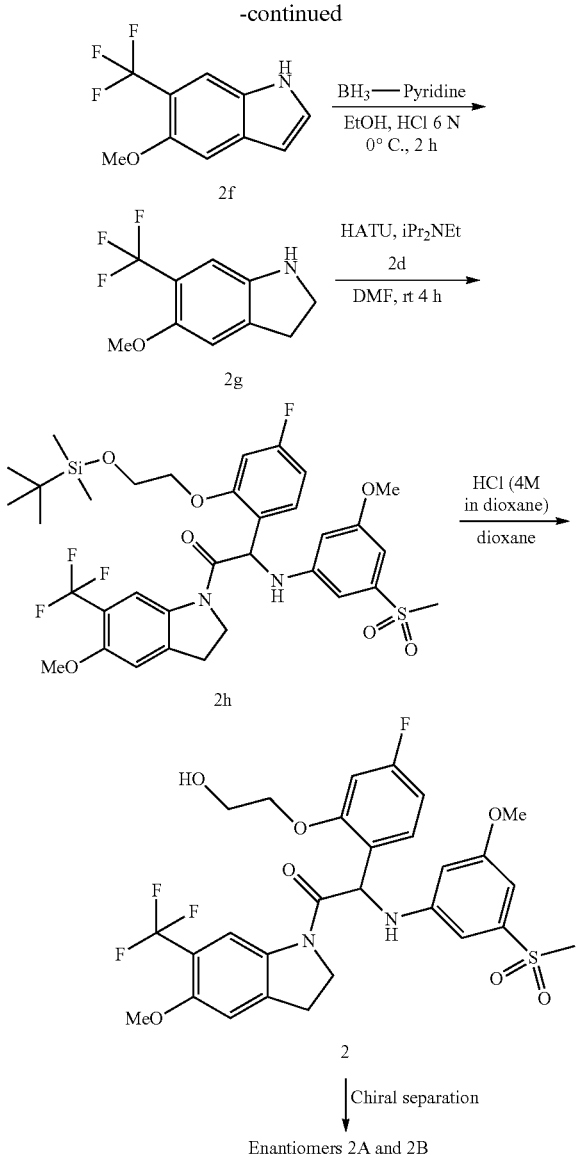

Synthesis of Intermediate 2a

To a mixture of ethyl 2-(4-fluoro-2-hydroxyphenyl)acetate 1b (10.6 g, 53.5 mmol) and cesium carbonate (34.8 g, 106.9 mmol) in DMF (200 mL) at 10° C. was added (2-bromoethoxy)(tert-butyl)dimethylsilane [CAS 86864-60-0] (13.8 mL, 64.2 mmol). The reaction mixture was stirred at room temperature overnight. H₂O was added and the reaction mixture was extracted with EtOAc. The organic phase was dried over MgSO₄, filtered and concentrated under reduced pressure. The residue was purified by flash chromatography on silica gel (15-40 μM, 40 g, heptane/EtOAc 80/20). The pure fractions were combined and the solvent was removed under reduced pressure to give ethyl 2-(2-(2-((tert-butyldimethylsilyl)oxy)ethoxy)-4-fluorophenyl)acetate 2a (17.7 g).

Synthesis of Intermediate 2b

To a 1M lithium bis(trimethylsilyl)amide solution in THF (28.05 mL, 28.05 mmol) cooled at −78° C. was added a solution of ethyl 2-(2-(2-((tert-butyldimethylsilyl)oxy)ethoxy)-4-fluorophenyl)acetate 2a (5 g, 14.03 mmol) in THF (30 mL). After stirring for 1 h at −78° C., chlorotrimethylsilane (2.85 mL, 22.44 mmol) was added. The reaction mixture was stirred at −78° C. for 15 min. N-Bromosuccinimide (3 g, 16.83 mmol) in THF (30 mL) was added and stirring was continued at −55° C. for 2 h. The reaction mixture was poured out into H₂O and extracted twice with EtOAc. The organic phases were combined, dried over MgSO₄, filtered and concentrated under reduced pressure to give ethyl 2-bromo-2-(2-(2-((tert-butyldimethylsilyl)oxy)ethoxy)-4-fluorophenyl)acetate 2b (6.57 g) which was used in the next step without further purification.

Synthesis of Intermediate 2c

A mixture of ethyl 2-bromo-2-(2-(2-((tert-butyldimethylsilyl)oxy)ethoxy)-4-fluorophenyl)acetate 2b (3 g, 6.89 mmol), 3-methoxy-5-(methylsulfonyl)aniline [CAS 62606-02-4] (2.08 g, 10.3 mmol) and diisopropylethylamine (2.37 mL, 13.8 mmol) in CH₃CN (60 mL) was stirred at 50° C. overnight. The reaction mixture was concentrated under reduced pressure. The residue was taken up with EtOAc and washed with 0.5N HCl and water. The organic phase was dried over MgSO₄, filtered and concentrated under reduced pressure. The residue was purified by flash chromatography on silica gel (15-40 μM, 120 g, heptane/EtOAc 90/10 to 80/20) to give ethyl 2-(2-(2-((tert-butyldimethylsilyl)oxy)ethoxy)-4-fluorophenyl)-2-((3-methoxy-5-(methylsulfonyl)phenyl)amino)acetate 2c (2.6 g).

Synthesis of Intermediate 2d

Lithium hydroxide monohydrate (205 mg, 4.8 mmol) was added portionwise to a solution of ethyl 2-(2-(2-((tert-butyldimethylsilyl)oxy)ethoxy)-4-fluorophenyl)-2-((3-methoxy-5-(methylsulfonyl)phenyl)amino)acetate 2c (2.227 g, 4.09 mmol) in THF/CH₃OH/H₂O (1/1/1) (100 mL) at 10° C. The reaction was stirred at room temperature for 4 h, and diluted with water. After cooling to 0° C., the solution was slowly acidified to pH 6 with 0.5 N HCl, and extracted with EtOAc. The organic layer was dried over MgSO₄, filtered and the solvent was concentrated under reduced pressure to give 2-(2-(2-((tert-butyldimethylsilyl)oxy)ethoxy)-4-fluorophenyl)-2-((3-methoxy-5-(methylsulfonyl)phenyl)amino) acetic acid 2d (2 g). The compound was used in the next step without further purification.

Synthesis of Intermediate 2e

A mixture of 1-methoxy-4-nitro-2-(trifluoromethyl)benzene [CAS 654-76-2] (24.5 g, 110.8 mmol) and 4-chlorophenoxyacetonitrile [CAS 3598-13-8] (20.4 g, 121.9 mmol) in DMF (100 mL) was added dropwise over 30 min to a stirred solution of tBuOK (27.35 g, 243.7 mmol) in DMF (100 mL) at −10° C. After addition, the purple solution was maintained at −10° C. for 1 h. 500 mL of ice-water and 500 mL of 6N HCl were added and the precipitate was filtered off, washed with water and dried under reduced pressure to afford 40.4 g of 2-(5-methoxy-2-nitro-4-(trifluoromethyl)phenyl)acetonitrile 2e (used as such in the next step).

Synthesis of Intermediate 2f

A solution of 2-(5-methoxy-2-nitro-4-(trifluoromethyl)phenyl)acetonitrile 2e (26 g, 99.9 mmol) in ethanol/water (9/1) (500 mL) and AcOH (5.2 mL) was hydrogenated for 1 h at a pressure of 3.5 Bar with 10% Pd/C (15.3 g) as the catalyst. The reaction mixture was filtered through a pad of Celite® and the filter cake was washed with a solvent mixture of $CH_2Cl_2$ and $CH_3OH$. The filtrate was concentrated under reduced pressure. The residue was filtered through a glass filter charged with silica 60-200 µm using heptane/EtOAc 80/20 as the eluent. The fractions containing the expected compound were combined and the solvent was concentrated under reduced pressure to give 5-methoxy-6-(trifluoromethyl)-1H-indole 2f (15.6 g).

Synthesis of Intermediate 2g

At 0° C., $BH_3$-Pyridine (23.5 mL, 232.4 mmol) was added dropwise to a solution of 5-methoxy-6-(trifluoromethyl)-1H-indole 2f (10 g, 46.5 mmol) in EtOH (60 mL). 6N HCl (140 mL) was slowly added while maintaining the temperature below 10° C. The mixture was stirred at 0° C. for 2 h. Water (200 mL) was added and the mixture was basified to pH 8-9 with a concentrated aqueous solution of NaOH (the reaction temperature was kept below 20° C.). The precipitate was filtered off, washed with water (twice) and co-evaporated under reduced pressure with toluene to give 5-methoxy-6-(trifluoromethyl)indoline 2g (9 g).

Synthesis of Intermediate 2h

To a solution of 2-(2-(2-((tert-butyldimethylsilyl)oxy)ethoxy)-4-fluorophenyl)-2-((3-methoxy-5-(methylsulfonyl)phenyl)amino)acetic acid 2d (1 g, 1.90 mmol) in DMF (10 mL) were added HATU (1.08 g, 2.84 mmol), diisopropylethylamine (940 µL, 5.69 mmol) and 5-methoxy-6-(trifluoromethyl)indoline 2g (412 mg, 1.90 mmol). The reaction mixture was stirred at room temperature for 4 h. The reaction mixture was diluted with water. The precipitate was filtered off, washed with water and taken up with EtOAc. The organic layer was washed with 1N HCl, water, dried over $MgSO_4$, filtered and the solvent was concentrated under reduced pressure to give 2-(2-(2-((tert-butyldimethylsilyl)oxy)ethoxy)-4-fluorophenyl)-2-((3-methoxy-5-(methylsulfonyl)phenyl)amino)-1-(5-methoxy-6-(trifluoromethyl)indolin-1-yl)ethanone 2h (1.36 g, purity by LC: 70%). The crude compound was used directly in the next reaction step.

Synthesis of Compound 2 and Chiral Separation into Enantiomers 2A and 2B

A solution of 2-(2-(2-((tert-butyldimethylsilyl)oxy)ethoxy)-4-fluorophenyl)-2-((3-methoxy-5-(methylsulfonyl)phenyl)amino)-1-(5-methoxy-6-(trifluoromethyl)indolin-1-yl)ethanone 2h (1.29 g, 1.77 mmol) in HCl 4M in dioxane (30 mL) and dioxane (100 mL) was stirred at room temperature for 1 h. The solvent was removed under reduced pressure. EtOAc and a 10% aqueous solution of $K_2CO_3$ were added. The organic phase was separated, dried over $MgSO_4$, filtered and the solvent was concentrated under reduced pressure. The residue was purified by flash chromatography on silica gel (15-40 µm, 80 g, $CH_2Cl_2$/MeOH/$NH_4OH$ 99/1/0.1) to give, after crystallization from $CH_3CN$, 2-(4-fluoro-2-(2-hydroxyethoxy)phenyl)-2-((3-methoxy-5-(methylsulfonyl)phenyl)amino)-1-(5-methoxy-6-(trifluoromethyl)indolin-1-yl)ethanone (Compound 2, 595 mg) as a racemate. The Enantiomers of Compound 2 (560 mg) were separated via Preparative Chiral SFC (Stationary phase: Whelk O1 (S,S)® 5 µm 250×21.1 mm, Mobile phase: 50% $CO_2$, 50% EtOH (+0.3% iPrNH$_2$)). The first eluted enantiomer (288 mg) was crystallized from $CH_3CN$/diisopropyl ether to give Enantiomer 2A (240 mg). The second eluted enantiomer (293 mg) was crystallized from $CH_3CN$/diisopropyl ether to give Enantiomer 2B (232 mg).

Compound 2:
$^1$H NMR (500 MHz, DMSO-$d_6$) δ ppm 3.09 (s, 3H) 3.12-3.29 (m, 2H) 3.73 (s, 3H) 3.74-3.80 (m, 1H) 3.80-3.90 (m, 4H) 4.02 (td, J=10.4, 7.2 Hz, 1H) 4.05-4.17 (m, 2H) 4.42 (td, J=10.4, 6.2 Hz, 1H) 4.97 (t, J=5.7 Hz, 1H) 5.79 (d, J=8.20 Hz, 1H) 6.56 (s, 1H) 6.61 (s, 1H) 6.78 (td, J=8.51, 2.52 Hz, 1H) 6.90 (s, 1H) 6.95-7.04 (m, 2H) 7.24 (s, 1H) 7.37 (dd, J=8.67, 6.78 Hz, 1H) 8.35 (s, 1H)

LC-MS (method LC-A): $R_t$ 3.02 min, MH$^+$ 613

Melting point: 215° C.

Enantiomer 2A:
$^1$H NMR (500 MHz, DMSO-$d_6$) δ ppm 3.09 (s, 3H) 3.12-3.29 (m, 2H) 3.73 (s, 3H) 3.74-3.80 (m, 1H) 3.80-3.90 (m, 4H) 4.02 (td, J=10.4, 7.2 Hz, 1H) 4.05-4.17 (m, 2H) 4.42 (td, J=10.4, 6.2 Hz, 1H) 4.97 (t, J=5.7 Hz, 1H) 5.79 (d, J=8.20 Hz, 1H) 6.56 (s, 1H) 6.61 (s, 1H) 6.78 (td, J=8.51, 2.52 Hz, 1H) 6.90 (s, 1H) 6.95-7.04 (m, 2H) 7.24 (s, 1H) 7.37 (dd, J=8.67, 6.78 Hz, 1H) 8.35 (s, 1H)

LC/MS (method LC-A): $R_t$ 3.00 min, MH$^+$ 613

$[\alpha]_D^{20}$: +53.5° (c 0.2392, DMF)

Chiral SFC (method SFC-B): $R_t$ 1.43 min, MH$^+$ 613, chiral purity 100%.

Melting point: 204° C.

Enantiomer 2B:
$^1$H NMR (500 MHz, DMSO-$d_6$) δ ppm 3.09 (s, 3H) 3.12-3.29 (m, 2H) 3.73 (s, 3H) 3.74-3.80 (m, 1H) 3.80-3.90 (m, 4H) 4.02 (td, J=10.4, 7.2 Hz, 1H) 4.05-4.17 (m, 2H) 4.42 (td, J=10.4, 6.2 Hz, 1H) 4.97 (t, J=5.7 Hz, 1H) 5.79 (d, J=8.20 Hz, 1H) 6.56 (s, 1H) 6.61 (t, J=1.73 Hz, 1H) 6.78 (td, J=8.51, 2.52 Hz, 1H) 6.90 (s, 1H) 6.95-7.04 (m, 2H) 7.24 (s, 1H) 7.37 (dd, J=8.67, 6.78 Hz, 1H) 8.35 (s, 1H)

LC/MS (method LC-A): $R_t$ 3.00 min, MH$^+$ 613

$[\alpha]_D^{20}$: −56.5° (c 0.255, DMF)

Chiral SFC (method SFC-B): $R_t$ 1.72 min, MH$^+$ 613, chiral purity 99.8%.

Melting point: 206° C.

Example 3: Synthesis of 2-(4-fluoro-2-(2-hydroxyethoxy)phenyl)-2-((3-methoxy-5-(methylsulfonyl)phenyl)amino)-1-(6-(trifluoromethoxy)indolin-1-yl)ethanone (Compound 3) and Chiral Separation into Enantiomers 3A and 3B

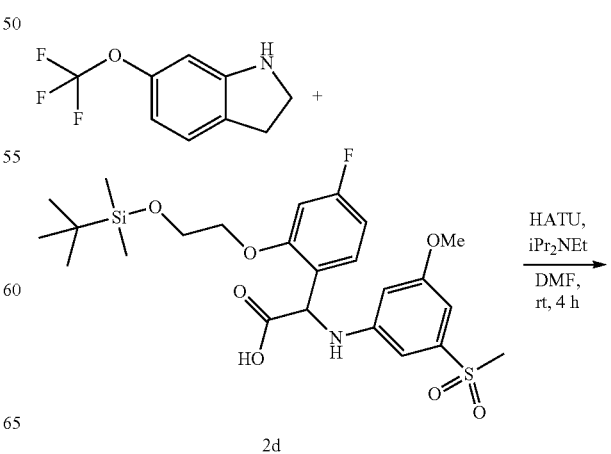

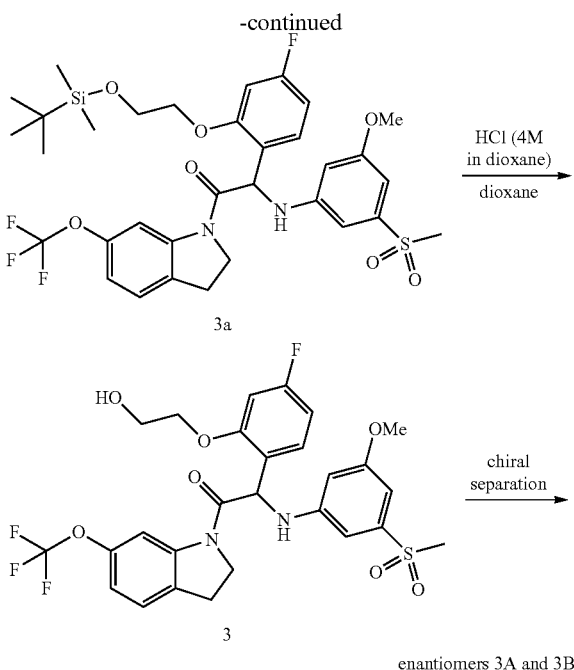

Synthesis of Intermediate 3a

To a solution of 2-(2-(2-((tert-butyldimethylsilyl)oxy)ethoxy)-4-fluorophenyl)-2-((3-methoxy-5-(methylsulfonyl)phenyl)amino)acetic acid 2d (1 g, 1.90 mmol) in DMF (10 mL) were added HATU (1.08 g, 2.84 mmol), diisopropylethylamine (940 µL, 5.69 mmol) and 6-(trifluoromethoxy)indoline [CAS 959235-95-1] (385 mg, 1.90 mmol). The reaction mixture was stirred at room temperature for 4 h. The reaction mixture was diluted with water. The precipitate was filtered off, washed with water and taken up with EtOAc. The organic layer was washed with a 10% solution of $K_2CO_3$ in water, a saturated solution of NaCl in water, water, dried over $MgSO_4$, filtered and the solvent was concentrated under reduced pressure to give 2-(2-(2-((tert-butyldimethylsilyl)oxy)ethoxy)-4-fluorophenyl)-2-((3-methoxy-5-(methylsulfonyl)phenyl)amino)-1-(6-(trifluoromethoxy)indolin-1-yl)ethanone 3a (1.32 g). The crude compound was used without purification in the next reaction step.

Synthesis of Compound 3 and Chiral Separation into Enantiomers 3A and 3B

A solution of 2-(2-(2-((tert-butyldimethylsilyl)oxy)ethoxy)-4-fluorophenyl)-2-((3-methoxy-5-(methylsulfonyl)phenyl)amino)-1-(6-(trifluoromethoxy)indolin-1-yl)ethanone 3a (1.17 g, 1.64 mmol) in HCl 4M in dioxane (3.3 mL) and dioxane (50 mL) was stirred at room temperature for 1h. The solvent was removed by evaporation under reduced pressure. EtOAc and a 10% solution of $K_2CO_3$ in water were added. The organic phase was separated, dried over $MgSO_4$, filtered and the solvent was concentrated under reduced pressure. The residue was purified by flash chromatography on silica gel (15-40 µm, 40 g, $CH_2Cl_2$/MeOH 99.5/0.5) to give 2-(4-fluoro-2-(2-hydroxyethoxy)phenyl)-2-((3-methoxy-5-(methylsulfonyl)phenyl)amino)-1-(6-(trifluoromethoxy)indolin-1-yl)ethanone (Compound 3, 508 mg) as a racemate. An analytical sample of Compound 3 was solidified from $CH_3CN$/diisopropyl ether (35 mg). The remaining amount was used to separate the enantiomers of Compound 3 via Preparative Chiral SFC (Stationary phase: Chiralpak® AD-H 5 µm 250×20 mm, Mobile phase: 70% $CO_2$, 30% EtOH (+0.3% iPrNH$_2$)). The first eluted enantiomer (166 mg) was solidified from heptane/diisopropyl ether to give Enantiomer 3A (130 mg). The second eluted enantiomer (165 mg) was solidified in heptane/diisopropyl ether to give Enantiomer 3B (110 mg).

Compound 3:

$^1$H NMR (500 MHz, DMSO-d$_6$) δ ppm 3.10 (s, 3H) 3.11-3.25 (m, 2H) 3.73 (s, 3H) 3.74-3.79 (m, 1H) 3.79-3.88 (m, 1H) 3.96-4.19 (m, 3H) 4.45 (dt, J=6.3, 10.4 Hz, 1H) 4.95 (t, J=5.52 Hz, 1H) 5.81 (d, J=8.51 Hz, 1H) 6.57 (s, 1H) 6.62 (t, J=1.89 Hz, 1H) 6.80 (td, J=8.43, 2.36 Hz, 1H) 6.91 (s, 1H) 6.96-7.05 (m, 3H) 7.28-7.46 (m, 2H) 8.05 (s, 1H)

LC-MS (method LC-A): R$_t$ 3.15 min, MH$^+$ 599

Enantiomer 3A:

$^1$H NMR (500 MHz, DMSO-d$_6$) δ ppm 3.10 (s, 3H) 3.11-3.25 (m, 2H) 3.73 (s, 3H) 3.74-3.79 (m, 1H) 3.79-3.88 (m, 1H) 3.96-4.19 (m, 3H) 4.45 (dt, J=6.3, 10.4 Hz, 1H) 4.97 (t, J=5.52 Hz, 1H) 5.81 (d, J=8.51 Hz, 1H) 6.57 (s, 1H) 6.62 (t, J=1.89 Hz, 1H) 6.80 (td, J=8.43, 2.36 Hz, 1H) 6.91 (s, 1H) 6.96-7.11 (m, 3H) 7.28-7.46 (m, 2H) 8.05 (s, 1H)

LC/MS (method LC-A): R$_t$ 3.13 min, MH$^+$ 599

$[α]_D^{20}$: −59.0° (c 0.2542, DMF)

Chiral SFC (method SFC-C): R$_t$ 1.87 min, MH$^+$ 599, chiral purity 100%.

Enantiomer 3B:

$^1$H NMR (500 MHz, DMSO-d$_6$) δ ppm 3.10 (s, 3H) 3.11-3.25 (m, 2H) 3.73 (s, 3H) 3.74-3.79 (m, 1H) 3.79-3.88 (m, 1H) 3.96-4.19 (m, 3H) 4.45 (dt, J=6.3, 10.4 Hz, 1H) 4.97 (t, J=5.52 Hz, 1H) 5.81 (d, J=8.51 Hz, 1H) 6.57 (s, 1H) 6.62 (t, J=1.89 Hz, 1H) 6.80 (td, J=8.43, 2.36 Hz, 1H) 6.91 (s, 1H) 6.96-7.11 (m, 3H) 7.28-7.46 (m, 2H) 8.05 (s, 1H)

LC/MS (method LC-A): R$_t$ 3.13 min, MH$^+$ 599

$[α]_D^{20}$: +56.8° (c 0.2467, DMF)

Chiral SFC (method SFC-C): R$_t$ 2.34 min, MH$^+$ 599, chiral purity 100%.

Example 4 (Method 1): Synthesis of 2-(4-chloro-2-(2-hydroxyethoxy)phenyl)-2-((3-methoxy-5-(methylsulfonyl)phenyl)amino)-1-(6-(trifluoromethyl)indolin-1-yl)ethanone (Compound 4)

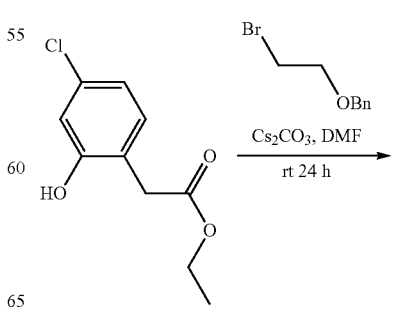

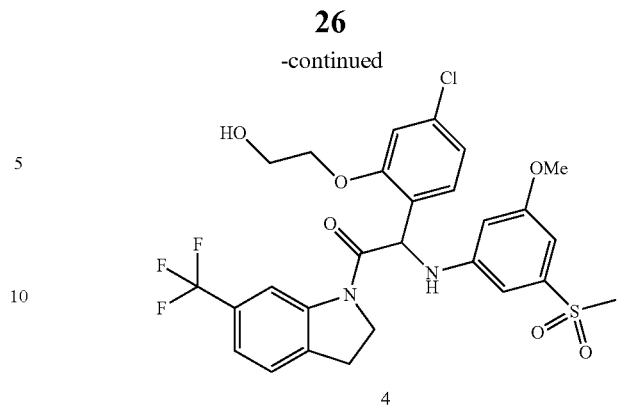

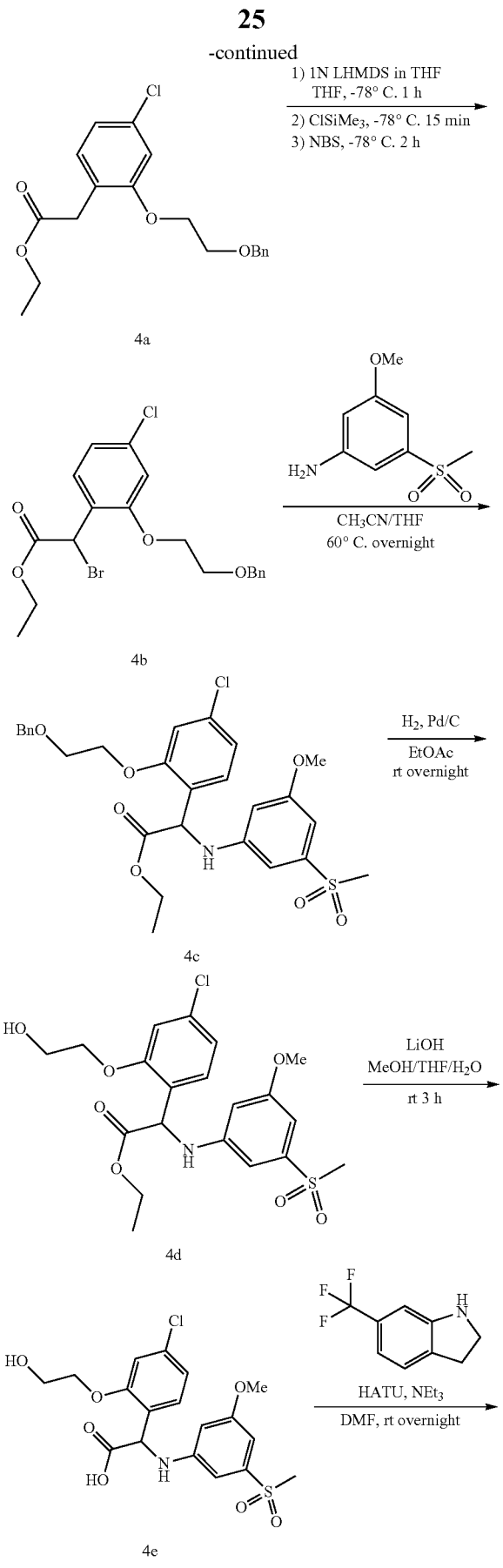

Synthesis of Intermediate 4a

To a mixture of ethyl 2-(4-chloro-2-hydroxyphenyl)acetate [CAS 1261826-30-5](2.82 g, 3.28 mmol) and cesium carbonate (8.56 g, 26.3 mmol) in DMF (50 mL) was added benzyl 2-bromoethyl ether [CAS 1462-37-9] (2.29 g, 14.5 mmol). The reaction mixture was stirred at room temperature for 24 h. H$_2$O was added and the reaction mixture was extracted with EtOAc. The organic phase was dried over Na$_2$SO$_4$, filtered and concentrated under reduced pressure. The residue was purified by flash chromatography on silica gel using a gradient of EtOAc (2% to 20%) in heptane to give ethyl 2-(2-(2-(benzyloxy)ethoxy)-4-chlorophenyl)acetate 4a (4.17 g).

Synthesis of Intermediate 4b

To a cooled (−78° C.) solution of 1M lithium bis(trimethylsilyl)amide in THF (11.0 mL, 11.0 mmol) was added a solution of ethyl 2-(2-(2-(benzyloxy)ethoxy)-4-chlorophenyl)acetate 4a (1.82 g, 5.22 mmol) in THF (9 mL). After stirring for 1 h at −78° C., chlorotrimethylsilane (1.1 mL, 8.67 mmol) was added. The reaction mixture was stirred at −78° C. for 15 min. N-Bromosuccinimide (1.11 g, 8.67 mmol) was added and stirring was continued at −78° C. for 2 h. The reaction mixture was poured out into H$_2$O and extracted with EtOAc. The organic phase was dried over MgSO$_4$, filtered and concentrated under reduced pressure to give ethyl 2-(2-(2-(benzyloxy)ethoxy)-4-chlorophenyl)-2-bromoacetate 4b (2.23 g) which was used in the next step without further purification.

Synthesis of Intermediate 4c

To a solution of ethyl 2-(2-(2-(benzyloxy)ethoxy)-4-chlorophenyl)-2-bromoacetate 4b (2.23 g, 5.22 mmol) in CH$_3$CN (22.5 mL) and THF (22.5 mL) was added 3-methoxy-5-(methylsulfonyl)aniline [CAS 62606-02-4] (3.12 g, 15.5 mmol). The reaction mixture was stirred at 60° C. overnight. The reaction mixture was concentrated under reduced pressure. The residue was partitioned between EtOAc and 1N HCl. The aqueous phase was extracted with EtOAc. The organic phases were combined, dried over MgSO$_4$, filtered and concentrated under reduced pressure. The residue was purified by flash chromatography on silica gel using a gradient of EtOAc (0% to 40%) in heptane to give ethyl 2-(2-(2-(benzyloxy)ethoxy)-4-chlorophenyl)-2-((3-methoxy-5-(methylsulfonyl) phenyl)amino)acetate 4c (1.57 g).

Synthesis of Intermediate 4d

A mixture of ethyl 2-(2-(2-(benzyloxy)ethoxy)-4-chlorophenyl)-2-((3-methoxy-5-(methylsulfonyl)phenyl)amino) acetate 4c (1.57 g, 2.86 mmol) and 10% palladium on carbon (0.320 g) in EtOAc (40 mL) was stirred overnight at room temperature under $H_2$ atmosphere. The reaction mixture was filtered through Celite®. The filtrate was concentrated under reduced pressure. The residue was purified by flash chromatography on silica gel using a gradient of EtOAc (30% to 100%) in heptane to give ethyl 2-(4-chloro-2-(2-hydroxyethoxy)phenyl)-2-((3-methoxy-5-(methylsulfonyl)phenyl) amino) acetate 4d (1.13 g).

Synthesis of Intermediate 4e

To a solution of ethyl 2-(4-chloro-2-(2-hydroxyethoxy) phenyl)-2-((3-methoxy-5-(methylsulfonyl)phenyl)amino) acetate 4d (1.14 g, 2.49 mmol) in THF (8 mL), MeOH (8 mL) and $H_2O$ (8 mL) was added lithium hydroxide monohydrate (0.522 g, 12.5 mmol). The reaction mixture was stirred at room temperature for 3 h. 1N HCl and EtOAc were added and the phases were separated. The aqueous phase was extracted with EtOAc. The organic phases were combined, washed with brine, dried over $MgSO_4$, filtered and concentrated under reduced pressure to give quantitatively 2-(4-chloro-2-(2-hydroxyethoxy)phenyl)-2-((3-methoxy-5-(methylsulfonyl)phenyl)amino)acetic acid 4e which was used in the next step without further purification.

Synthesis of Compound 4

To a solution of 6-trifluromethylindoline [CAS 181513-29-1] (0.200 g, 1.07 mmol), 2-(4-chloro-2-(2-hydroxyethoxy)phenyl)-2-((3-methoxy-5-(methylsulfonyl)phenyl) amino)acetic acid 4e (0.478 g, 1.11 mmol) and triethylamine (0.593 mL, 4.28 mmol) in DMF (10 mL) was added HATU (0.406 g, 1.07 mmol). The reaction mixture was stirred overnight. The reaction mixture was diluted with $H_2O$ and was extracted with ethyl acetate. The organic phase was washed with 1N HCl, an aqueous saturated $NaHCO_3$ solution and brine, dried over $MgSO_4$, filtered and concentrated under reduced pressure. The residue was purified by flash chromatography on silica gel using a gradient of EtOAc (60% to 70%) in heptane. The fractions containing the desired product were combined and concentrated under reduced pressure. The residue was purified by flash chromatography on silica gel using a gradient of EtOAc (0% to 25%) in $CH_2Cl_2$ to give 2-(4-chloro-2-(2-hydroxyethoxy) phenyl)-2-((3-methoxy-5-(methylsulfonyl)phenyl)amino)-1-(6-(trifluoromethyl)indolin-1-yl)ethan-1-one (Compound 4, 0.162 g) as a racemic mixture.

Compound 4:

$^1$H NMR (300 MHz, DMSO-$d_6$) δ ppm 3.11 (s, 3H) 3.22 (m, 2H) 3.67-3.88 (m, 5H) 4.00-4.22 (m, 3H) 4.44 (m, 1H) 4.98 (t, J=5.5 Hz, 1H) 5.83 (d, J=8.3 Hz, 1H) 6.56 (s, 1H) 6.63 (s, 1H) 6.92 (s, 1H) 7.04 (m, 2H) 7.17 (m, 1H) 7.31-7.50 (m, 3H) 8.38 (s, 1H)

LC-MS (method LC-C): $R_t$ 1.89 min, MH$^+$ 599

Example 4 (Method 2): Synthesis of 2-(4-chloro-2-(2-hydroxyethoxy)phenyl)-2-((3-methoxy-5-(methylsulfonyl)phenyl)amino)-1-(6-(trifluoromethyl) indolin-1-yl)ethanone (Compound 4) and Chiral Separation into Enantiomers 4A and 4B

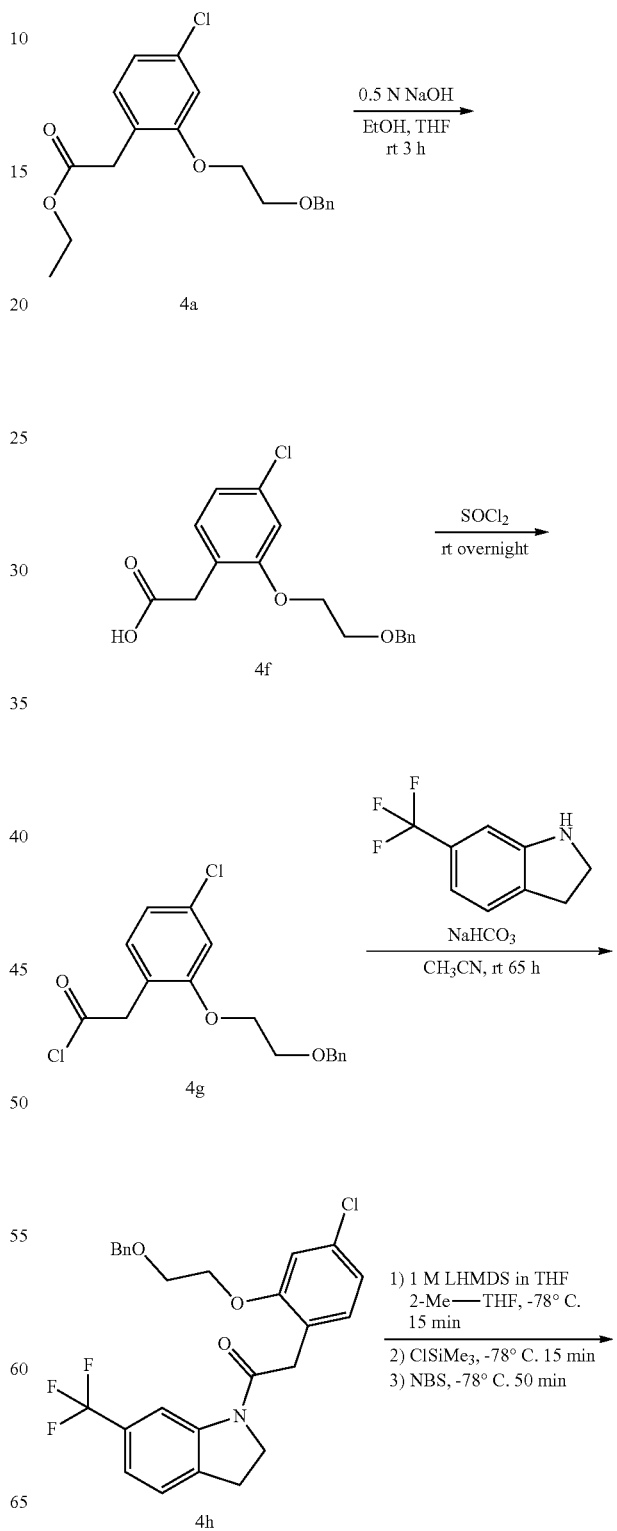

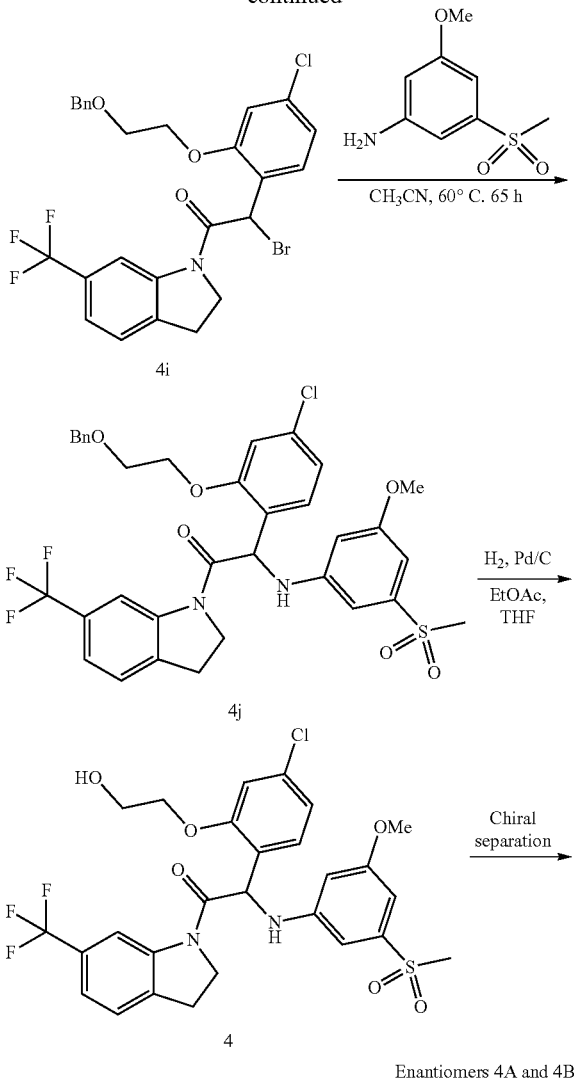

Synthesis of Intermediate 4f

To a solution of ethyl 2-(2-(2-(benzyloxy)ethoxy)-4-chlorophenyl)acetate 4a (4.17 g, 12.0 mmol) in a mixture of EtOH (80 mL) and THF (40 mL) was added 0.5N NaOH (72 mL, 36.0 mmol). The reaction mixture was stirred at room temperature for 3 h. The reaction mixture was partially concentrated under reduced pressure to remove the organic solvents. The residue was acidified to pH 2-3 with 1N HCl and the mixture was extracted with EtOAc. The organic phase was dried over MgSO$_4$, filtered and concentrated under reduced pressure to give 2-(2-(2-(benzyloxy)ethoxy)-4-chlorophenyl)acetic acid 4f (3.83 g).

Synthesis of Intermediate 4g

A solution of 2-(2-(2-(benzyloxy)ethoxy)-4-chlorophenyl)acetic acid 4f (7.12 g, 22.2 mmol) in thionyl chloride (50 mL, 689 mmol) was stirred at room temperature for 18 h. The reaction mixture was concentrated under reduced pressure and co-evaporated with toluene to give 2-(2-(2-(benzyloxy)ethoxy)-4-chlorophenyl)acetyl chloride 4g (7.53 g) which was used in the next step without further purification.

Synthesis of Intermediate 4h

A solution of 2-(2-(2-(benzyloxy)ethoxy)-4-chlorophenyl)acetyl chloride 4g (5.29 g, 15.6 mmol) in CH$_3$CN (50 mL) was added dropwise under N$_2$-atm to a stirring mixture of 6-(trifluoromethyl)indoline [CAS 181513-29-1] (2.92 g, 15.6 mmol) and sodium bicarbonate (1.44 g, 17.1 mmol) in CH$_3$CN (50 mL). The reaction mixture was stirred at room temperature for 65 h and poured out into water (500 mL). The product was extracted (2×) with Et$_2$O. The combined organic layers were washed with brine, dried over MgSO$_4$, filtered and evaporated under reduced pressure. The residue solidified upon standing. The product was stirred up in diisopropyl ether (25 mL), filtered off, washed (3×) with diisopropyl ether, and dried under vacuum at 45° C. to provide 2-(2-(2-(benzyloxy)ethoxy)-4-chlorophenyl)-1-(6-(trifluoromethyl)indol in-1-yl)ethanone 4h (6.97 g).

Synthesis of Intermediate 4i

A solution of 2-(2-(2-(benzyloxy)ethoxy)-4-chlorophenyl)-1-(6-(trifluoromethyl)indolin-1-yl)ethanone 4h (1.0 g, 2.04 mmol) in 2-Me-THF (100 mL) was stirred under N$_2$-flow and cooled to −78° C. A solution of 1M lithium bis(trimethylsilyl)amide in THF (4.08 mL, 4.08 mmol) was added dropwise and the resulting mixture was stirred at −78° C. for 15 minutes. Chlorotrimethylsilane (417 μL, 3.27 mmol) was added dropwise and the mixture was stirred at −78° C. for 15 minutes. A solution of N-bromosuccinimide (400 mg, 2.25 mmol) in 2-Me-THF (25 mL) was added dropwise and the reaction mixture was stirred at −78° C. for 50 min. An aqueous saturated solution of NH$_4$Cl (40 mL) was added at once, and the resulting mixture was stirred without cooling until the temperature reached 0° C. Water (10 mL) was added and the layers were separated. The organic layer was dried over MgSO$_4$, filtered, evaporated under reduced pressure, and co-evaporated with CH$_3$CN to provide 2-(2-(2-(benzyloxy)ethoxy)-4-chlorophenyl)-2-bromo-1-(6-(trifluoromethyl)indolin-1-yl)ethanone 4i (1.16 g). The product was used without further purification in the next step.

Synthesis of Intermediate 4j

To a stirred solution of 2-(2-(2-(benzyloxy)ethoxy)-4-chlorophenyl)-2-bromo-1-(6-(trifluoromethyl)indolin-1-yl) ethanone 4i (1.16 g, 2.04 mmol) in CH$_3$CN (50 mL) under N$_2$-atm were added 3-methoxy-5-(methylsulfonyl)aniline [CAS 62606-02-4] (0.82 g, 4.08 mmol), and diisopropylethylamine (703 μL, 4.08 mmol) and the reaction mixture was stirred at 60° C. for 65 h. The mixture was cooled to room temperature and poured out into stirring H$_2$O (250 mL). The product was extracted (2×) with Et$_2$O. The combined organic layers were dried over MgSO$_4$, filtered, and evaporated under reduced pressure. The residue was purified by flash chromatography on silica (40 g) using a gradient of heptane/EtOAc/EtOH 100/0/0 to 40/45/15. The desired fractions were combined and the solvent was evaporated under reduced pressure on a Rotavapor® to a residual volume of 35 mL. The product crystallized upon standing. The precipitate was filtered off, washed (3×) with EtOAc/heptane 1/1, and dried under vacuum at 45° C. to provide 2-(2-(2-(benzyloxy)ethoxy)-4-chlorophenyl)-2-((3-methoxy-5-

(methylsulfonyl)phenyl)amino)-1-(6-(trifluoromethyl)indolin-1-yl)ethanone 4j (870 mg).

Synthesis of Compound 4 and Chiral Separation into Enantiomers 4A and 4B

A solution of 2-(2-(2-(benzyloxy)ethoxy)-4-chlorophenyl)-2-((3-methoxy-5-(methylsulfonyl)phenyl)amino)-1-(6-(trifluoromethyl)indolin-1-yl)ethanone 4j (210 mg, 0.28 mmol) in THF (30 mL) was added to a stirring mixture of Pd/C (0.5 g) in EtOAc (10 mL). The mixture was hydrogenated for 10 min at room temperature under atmospheric pressure. The catalyst was removed by filtration over Dicalite® and the solvents were evaporated under reduced pressure. The residue was combined with another batch (total amount: 1.0 g) and purified via Reverse phase HPLC (Stationary phase: Kromasil C18 100A 5 um (Eka Nobel), Mobile phase: Gradient from 50% ammoniunbicarbonate (0.25% in water), 50% acetonitrile to 20% ammoniunbicarbonate (0.25% in water), 80% acetonitrile) yielding Compound 4 (700 mg). The enantiomers of Compound 4 (700 mg) were separated via Normal Phase Chiral separation (Stationary phase: Whelk-O1 (SS) 5 μm with recycling peak shaving technique, Mobile phase: 100% ethanol). The fractions containing the first eluted enantiomer were combined and evaporated under reduced pressure. The residue was further purified by flash chromatography on silica gel (4 g) using a gradient of heptane/EtOAc/EtOH 100/0/0 to 40/45/15. The desired fractions were combined and evaporated, and co-evaporated with MeOH. The residue was triturated at 45° C. in H$_2$O (4 mL) and MeOH (1 mL), the precipitate was filtered off, washed (3×) with H$_2$O/MeOH 4/1, and dried under vacuum at 45° C. to provide Enantiomer 4A (197 mg). The fractions containing the second eluted enantiomer were combined and evaporated under reduced pressure. The residue was further purified by flash chromatography on silica gel (4 g) using a gradient of heptane/EtOAc/EtOH 100/0/0 to 40/45/15. The desired fractions were combined and evaporated, and co-evaporated with MeOH/water. The residue was stirred up in H$_2$O (4 mL) and MeOH (1 mL), the precipitate was filtered off, washed (3×) with H$_2$O/MeOH 4/1, and dried under vacuum at 45° C. to provide Enantiomer 4B (209 mg).

Enantiomer 4A:
$^1$H NMR (400 MHz, DMSO-d$_6$) δ ppm 3.10 (s, 3H) 3.16-3.27 (m, 2H) 3.68-3.85 (m, 5H) 4.04-4.20 (m, 3H) 4.44 (td, J=10.2, 6.6 Hz, 1H) 4.94 (t, J=5.6 Hz, 1H) 5.83 (d, J=8.4 Hz, 1H) 6.56 (t, J=2.1 Hz, 1H) 6.63 (t, J=1.8 Hz, 1H) 6.91 (t, J=1.4 Hz, 1H) 6.97-7.08 (m, 2H) 7.17 (d, J=2.0 Hz, 1H) 7.36 (d, J=8.1 Hz, 1H) 7.39 (dd, J=7.9, 0.9 Hz, 1H) 7.43-7.49 (m, 1H) 8.38 (br s, 1H)
LC/MS (method LC-D): R$_t$ 1.17 min, MH$^+$ 599
$[α]_D^{20}$: +59.8° (c 0.435, DMF)
Chiral SFC (method SFC-I): R$_t$ 2.84 min, MH$^+$ 599, chiral purity 100%.

Enantiomer 4B:
$^1$H NMR (400 MHz, DMSO-d$_6$) δ ppm 3.10 (s, 3H) 3.16-3.26 (m, 2H) 3.70-3.85 (m, 5H) 4.02-4.19 (m, 3H) 4.44 (td, J=10.2, 6.4 Hz, 1H) 4.94 (t, J=5.6 Hz, 1H) 5.83 (d, J=8.4 Hz, 1H) 6.56 (t, J=2.0 Hz, 1H) 6.63 (t, J=1.8 Hz, 1H) 6.91 (t, J=1.7 Hz, 1H) 6.99-7.07 (m, 2H) 7.16 (d, J=2.0 Hz, 1H) 7.36 (d, J=8.1 Hz, 1H) 7.37-7.41 (m, 1H) 7.44-7.48 (m, 1H) 8.38 (s, 1H)
LC/MS (method LC-D): R$_t$ 1.17 min, MH$^+$ 599
$[α]_D^{20}$: −56.4° (c 0.47, DMF)
Chiral SFC (method SFC-I): R$_t$ 3.14 min, MH$^+$ 599, chiral purity 97.0%.

Example 5: Synthesis of 2-(4-chloro-2-(2-hydroxyethoxy)phenyl)-2-((3-methoxy-5-(methylsulfonyl)phenyl)amino)-1-(5-methoxy-6-(trifluoromethyl)indolin-1-yl)ethanone (Compound 5) and Chiral Separation into Enantiomers 5A and 5B

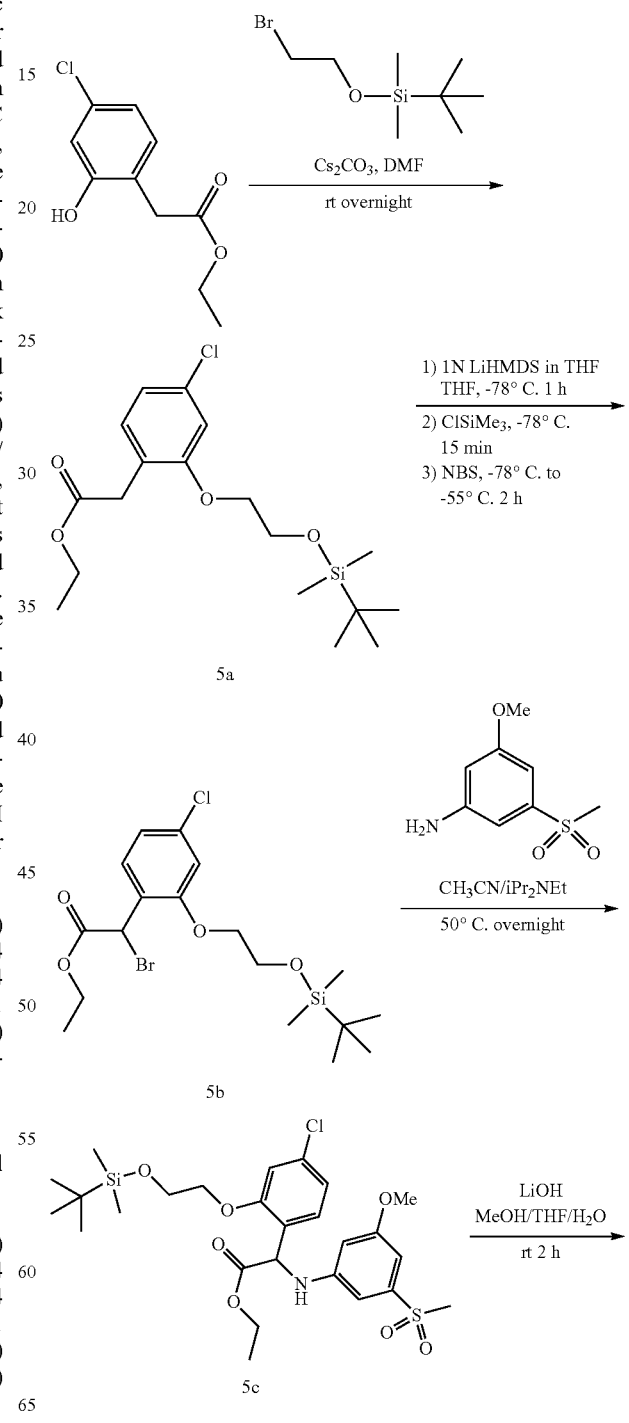

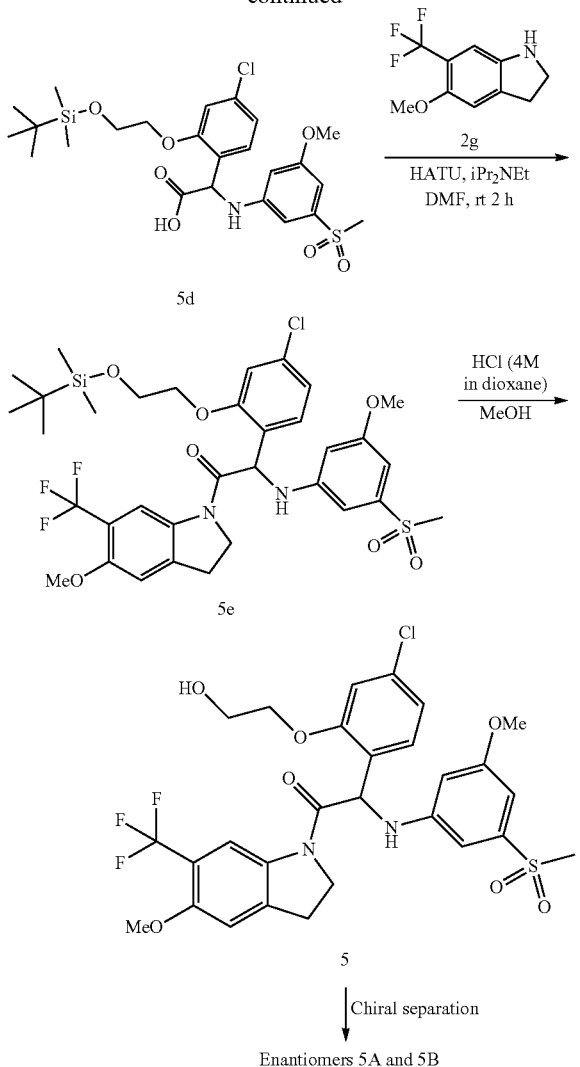

Synthesis of Intermediate 5a

To a mixture of ethyl 2-(4-chloro-2-hydroxyphenyl)acetate [CAS 1261826-30-5](5.2 g, 24.2 mmol) and cesium carbonate (15.8 g, 48.5 mmol) in DMF (90 mL) at 10° C. was added (2-bromoethoxy)(tert-butyl)dimethylsilane [CAS 86864-60-0](6.26 mL, 29.1 mmol). The reaction mixture was stirred at room temperature overnight. Water was added and the reaction mixture was extracted with EtOAc. The organic phase was dried over MgSO$_4$, filtered and concentrated under reduced pressure. The residue was purified by flash chromatography on silica gel (15-40 µm, 80 g, heptane/EtOAc 80/20). The pure fractions were combined and the solvent was removed under reduced pressure to give ethyl 2-(2-(2-((tert-butyldimethylsilyl)oxy)ethoxy)-4-chlorophenyl)acetate 5a (7.8 g).

Synthesis of Intermediate 5b

To a cooled (−78° C.) solution of 1M lithium bis(trimethylsilyl)amide in THF (41.8 mL, 41.8 mmol) was added a solution of ethyl 2-(2-(2-((tert-butyldimethylsilyl)oxy)ethoxy)-4-chlorophenyl)acetate 5a (7.8 g, 20.9 mmol) in THF (45 mL). After 1 h at −70° C., chlorotrimethylsilane (4.24 mL, 33.5 mmol) was added. The reaction mixture was stirred at −70° C. for 15 min. N-Bromosuccinimide (4.46 g, 25.1 mmol) in THF (45 mL) was added and stirring was continued at −55° C. for 2 h. The reaction mixture was poured out into H$_2$O and extracted twice with EtOAc. The organic phases were combined, dried over MgSO$_4$, filtered and concentrated under reduced pressure to give ethyl 2-bromo-2-(2-(2-((tert-butyldimethylsilyl)oxy)ethoxy)-4-chlorophenyl)acetate 5b (10.1 g) which was used in the next step without further purification.

Synthesis of Intermediate 5c

A mixture of ethyl 2-bromo-2-(2-(2-((tert-butyldimethylsilyl)oxy)ethoxy)-4-chlorophenyl)acetate 5b (4.75 g, 10.5 mmol), 3-methoxy-5-(methylsulfonyl)aniline [CAS 62606-02-4] (3.17 g, 15.8 mmol) and diisopropylethylamine (3.62 mL, 21.0 mmol) in CH$_3$CN (90 mL) was stirred at 50° C. overnight. The reaction mixture was concentrated under reduced pressure. The residue was taken up with EtOAc and washed with 0.5N HCl and water. The organic phase was dried over MgSO$_4$, filtered and concentrated under reduced pressure. The residue was purified by flash chromatography on silica gel (15-40 µm, 120 g, heptane/EtOAc 90/10 to 80/20) to give ethyl 2-(2-(2-((tert-butyldimethylsilyl)oxy)ethoxy)-4-chlorophenyl)-2-((3-methoxy-5-(methylsulfonyl)phenyl)amino)acetate 5c (3.5 g).

Synthesis of Intermediate 5d

Lithium hydroxide monohydrate (513 mg, 12.2 mmol) was added portionwise to a solution of ethyl 2-(2-(2-((tert-butyldimethylsilyl)oxy)ethoxy)-4-chlorophenyl)-2-((3-methoxy-5-(methylsulfonyl)phenyl)amino)acetate 5c (3.5 g, 6.12 mmol) in THF/CH$_3$OH/H$_2$O (1/1/1) (75 mL) at 10° C. The reaction was stirred at room temperature for 2 h, diluted with water and cooled to 0° C. The solution was slowly acidified to pH 6 with 0.5N HCl, and extracted with EtOAc. The organic layer was dried over MgSO$_4$, filtered and the solvent was concentrated under reduced pressure to give 2-(2-(2-((tert-butyldimethylsilyl)oxy)ethoxy)-4-chlorophenyl)-2-((3-methoxy-5-(methylsulfonyl)phenyl)amino)acetic acid 5d (2.85 g). The compound was used without further purification in the next step.

Synthesis of Intermediate 5e

To a solution of 2-(2-(2-((tert-butyldimethylsilyl)oxy)ethoxy)-4-chlorophenyl)-2-((3-methoxy-5-(methylsulfonyl)phenyl)amino)acetic acid 5d (1 g, 1.84 mmol) in DMF (10 mL) were added HATU (1.05 g, 2.76 mmol), diisopropylethylamine (913 µL, 5.53 mmol) and 5-methoxy-6-(trifluoromethyl)indoline 2g (412 mg, 1.90 mmol). The reaction mixture was stirred at room temperature for 2 h. The reaction mixture was diluted with water. The precipitate was filtered off, washed with water and taken up with EtOAc. The organic layer was washed with a 10% solution of K$_2$CO$_3$ and water, dried over MgSO$_4$, filtered and the solvent was concentrated under reduced pressure to give 2-(2-(2-((tert-butyldimethylsilyl)oxy)ethoxy)-4-chlorophenyl)-2-((3-methoxy-5-(methylsulfonyl)phenyl)amino)-1-(5-methoxy-6-(trifluoromethyl)indolin-1-yl)ethanone 5e (1.4 g). The compound was used without further purification in the next reaction step.

Synthesis of Compound 5 and Chiral Separation into Enantiomers 5A and 5B

Under N$_2$ flow at 5° C., HCl 4M in dioxane (4.71 mL, 18.8 mmol) was added dropwise to a solution of 2-(2-(2-((tert-butyldimethylsilyl)oxy)ethoxy)-4-chlorophenyl)-2-((3-methoxy-5-(methylsulfonyl)phenyl)amino)-1-(5-methoxy-6-(trifluoromethyl)indolin-1-yl)ethanone 5e (1.4 g, 1.88 mmol) in MeOH (25 mL). The reaction was stirred at room temperature for 1 h. The mixture was cooled to 0° C., basified with a 10% aqueous solution of K$_2$CO$_3$ and extracted with EtOAc. The organic phase was separated, dried over MgSO$_4$, filtered and the solvent was concentrated under reduced pressure. The residue was purified by flash chromatography on silica gel (15-40 μm, 40 g, CH$_2$Cl$_2$/MeOH 98.5/1.5). The pure fractions were combined and the solvent was removed under reduced pressure to give 2-(4-chloro-2-(2-hydroxyethoxy)phenyl)-2-((3-methoxy-5-(methylsulfonyl)phenyl)amino)-1-(5-methoxy-6-(trifluoromethyl)indolin-1-yl)ethanone (Compound 5, 1.0 g) as a racemate. An analytical sample of Compound 5 was crystallized from MeOH (60 mg). The remaining amount was used to separate the Enantiomers via Preparative Chiral SFC (Stationary phase: Chiralpak® IC 5 μm 250×30 mm, Mobile phase: 70% CO$_2$, 30% EtOH (+0.3% iPrNH$_2$)). The first eluted enantiomer (400 mg) was solidified from diisopropyl ether to give Enantiomer 5A (351 mg). The second eluted enantiomer (430 mg) was solidified from diisopropyl ether to give Enantiomer 5B (336 mg).

Compound 5:

$^1$H NMR (500 MHz, DMSO-d$_6$) δ ppm 3.10 (s, 3H) 3.13-3.27 (m, 2H) 3.73 (s, 3H) 3.73-3.78 (m, 1H) 3.78-3.84 (m, 1H) 3.84 (s, 3H) 3.98-4.22 (m, 3H) 4.41 (dt, J=6.1, 10.1 Hz, 1H) 4.95 (t, J=5.6 Hz, 1H) 5.80 (d, J=8.08 Hz, 1H) 6.55 (s, 1H) 6.61 (s, 1H) 6.90 (s, 1H) 6.96-7.05 (m, 2H) 7.16 (d, J=1.52 Hz, 1H) 7.24 (s, 1H) 7.35 (d, J=8.08 Hz, 1H) 8.34 (s, 1H)

LC-MS (method LC-A): R$_t$ 3.15 min, MH$^+$ 629

Melting point: 220° C.

Enantiomer 5A:

$^1$H NMR (400 MHz, DMSO-d$_6$) δ ppm 3.10 (s, 3H) 3.13-3.27 (m, 2H) 3.73 (s, 3H) 3.73-3.78 (m, 1H) 3.78-3.84 (m, 1H) 3.84 (s, 3H) 3.98-4.22 (m, 3H) 4.41 (dt, J=6.1, 10.1 Hz, 1H) 4.95 (t, J=5.6 Hz, 1H) 5.80 (d, J=8.08 Hz, 1H) 6.55 (s, 1H) 6.61 (s, 1H) 6.90 (s, 1H) 6.96-7.05 (m, 2H) 7.16 (d, J=1.52 Hz, 1H) 7.24 (s, 1H) 7.35 (d, J=8.08 Hz, 1H) 8.34 (s, 1H)

LC/MS (method LC-A): R$_t$ 3.13 min, MH$^+$ 629

[α]$_D^{20}$: −60.4° (c 0.28, DMF)

Chiral SFC (method SFC-D): R$_t$ 1.02 min, MH$^+$ 629, chiral purity 100%.

Enantiomer 5B:

$^1$H NMR (400 MHz, DMSO-d$_6$) δ ppm 3.10 (s, 3H) 3.13-3.27 (m, 2H) 3.73 (s, 3H) 3.73-3.78 (m, 1H) 3.78-3.84 (m, 1H) 3.84 (s, 3H) 3.98-4.22 (m, 3H) 4.41 (dt, J=6.1, 10.1 Hz, 1H) 4.95 (brt, J=5.6 Hz, 1H) 5.80 (d, J=8.08 Hz, 1H) 6.55 (s, 1H) 6.61 (s, 1H) 6.90 (s, 1H) 6.96-7.05 (m, 2H) 7.16 (d, J=1.52 Hz, 1H) 7.24 (s, 1H) 7.35 (d, J=8.08 Hz, 1H) 8.34 (s, 1H)

LC/MS (method LC-A): R$_t$ 3.15 min, MH$^+$ 629

[α]$_D^{20}$: +56.7° (c 0.3, DMF)

Chiral SFC (method SFC-D): R$_t$ 1.22 min, MH$^+$ 629, chiral purity 99.7%.

Example 6 (Method 1): Synthesis of 2-(4-chloro-2-(2-hydroxyethoxy)phenyl)-2-((3-methoxy-5-(methylsulfonyl)phenyl)amino)-1-(6-(trifluoromethoxy)indolin-1-yl)ethanone (Compound 6)

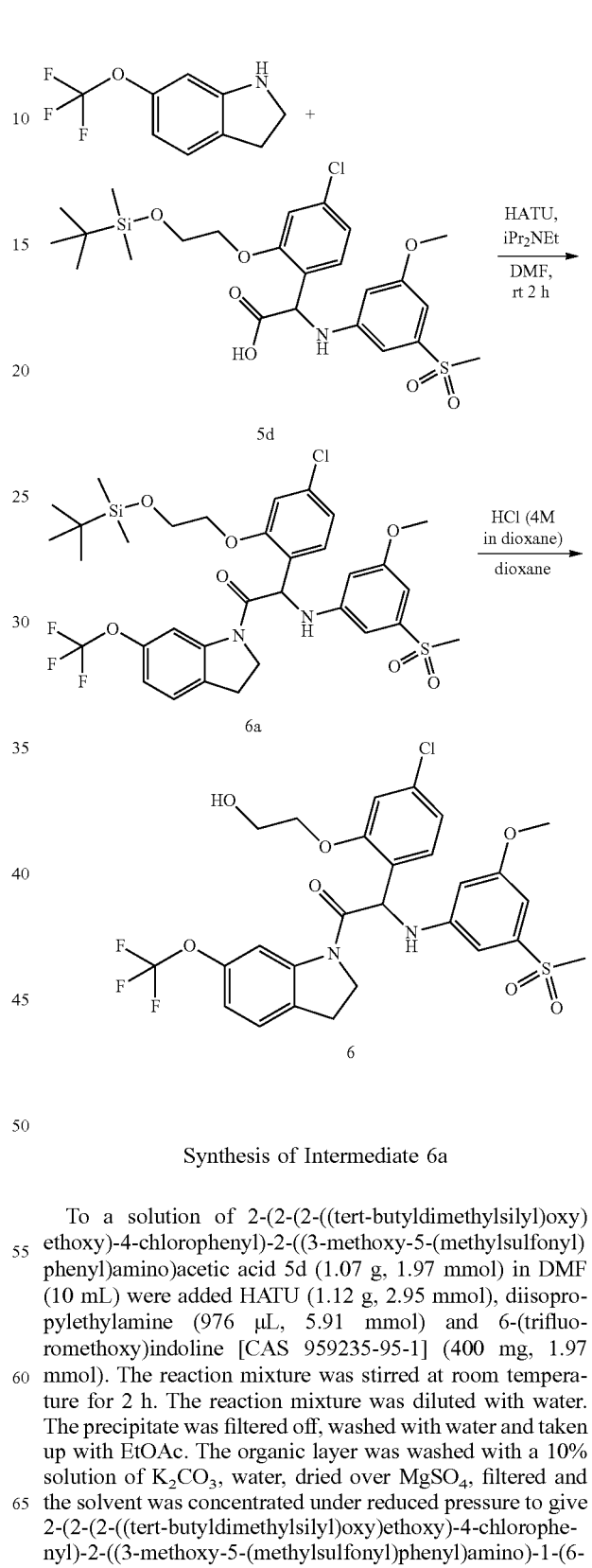

Synthesis of Intermediate 6a

To a solution of 2-(2-(2-((tert-butyldimethylsilyl)oxy)ethoxy)-4-chlorophenyl)-2-((3-methoxy-5-(methylsulfonyl)phenyl)amino)acetic acid 5d (1.07 g, 1.97 mmol) in DMF (10 mL) were added HATU (1.12 g, 2.95 mmol), diisopropylethylamine (976 μL, 5.91 mmol) and 6-(trifluoromethoxy)indoline [CAS 959235-95-1] (400 mg, 1.97 mmol). The reaction mixture was stirred at room temperature for 2 h. The reaction mixture was diluted with water. The precipitate was filtered off, washed with water and taken up with EtOAc. The organic layer was washed with a 10% solution of K$_2$CO$_3$, water, dried over MgSO$_4$, filtered and the solvent was concentrated under reduced pressure to give 2-(2-(2-((tert-butyldimethylsilyl)oxy)ethoxy)-4-chlorophenyl)-2-((3-methoxy-5-(methylsulfonyl)phenyl)amino)-1-(6-

(trifluoromethoxy)indolin-1-yl)ethanone 6a (1.36 g). The crude compound was used without purification in the next reaction step.

Synthesis of Compound 6

Under N$_2$ flow at 5° C., HCl 4M in dioxane (4.66 mL, 18.6 mmol) was added dropwise to a solution of 2-(2-(2-((tert-butyldimethylsilyl)oxy)ethoxy)-4-chlorophenyl)-2-((3-methoxy-5-(methylsulfonyl)phenyl)amino)-1-(6-(trifluoromethoxy)indolin-1-yl)ethanone 6a (1.36 g, 1.87 mmol) in MeOH (25 mL). The reaction was stirred at room temperature for 1 h. The mixture was cooled to 0° C., basified with a 10% aqueous solution of K$_2$CO$_3$ and extracted with EtOAc. The organic phase was separated, dried over MgSO$_4$, filtered and the solvent was concentrated under reduced pressure. The residue was purified by flash chromatography on silica gel (15-40 µm, 40 g, CH$_2$Cl$_2$/MeOH 99.5/0.5). The pure fractions were combined and the solvent was removed under reduced pressure to give 2-(4-chloro-2-(2-hydroxyethoxy)phenyl)-2-((3-methoxy-5-(methylsulfonyl)phenyl)amino)-1-(6-(trifluoromethoxy)indolin-1-yl)ethanone (Compound 6, 540 mg) as a racemate. An analytical sample of Compound 6 was obtained by crystallization from MeOH (34 mg).

Compound 6:
$^1$H NMR (400 MHz, DMSO-d$_6$) δ ppm 3.07-3.23 (m, 5H) 3.70-3.83 (m, 5H) 4.06-4.19 (m, 3H) 4.42 (td, J=10.23, 6.32 Hz, 1H) 4.92 (t, J=5.31 Hz, 1H) 5.81 (d, J=8.59 Hz, 1H) 6.56 (s, 1H) 6.61 (s, 1H) 6.90 (s, 1H) 6.99-7.05 (m, 3H) 7.16 (d, J=2.02 Hz, 1H) 7.30-7.40 (m, 2H) 8.03 (s, 1H) LC-MS (method LC-A): R$_t$ 3.28 min, MH$^+$ 615

Melting point: 191° C.

Example 6 (Method 2): Synthesis of 2-(4-chloro-2-(2-hydroxyethoxy)phenyl)-2-((3-methoxy-5-(methylsulfonyl)phenyl)amino)-1-(6-(trifluoromethoxy)indolin-1-yl)ethanone (Compound 6) and Chiral Separation into Enantiomers 6A and 6B

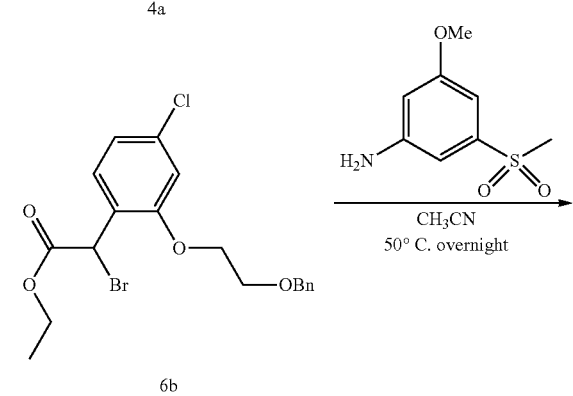

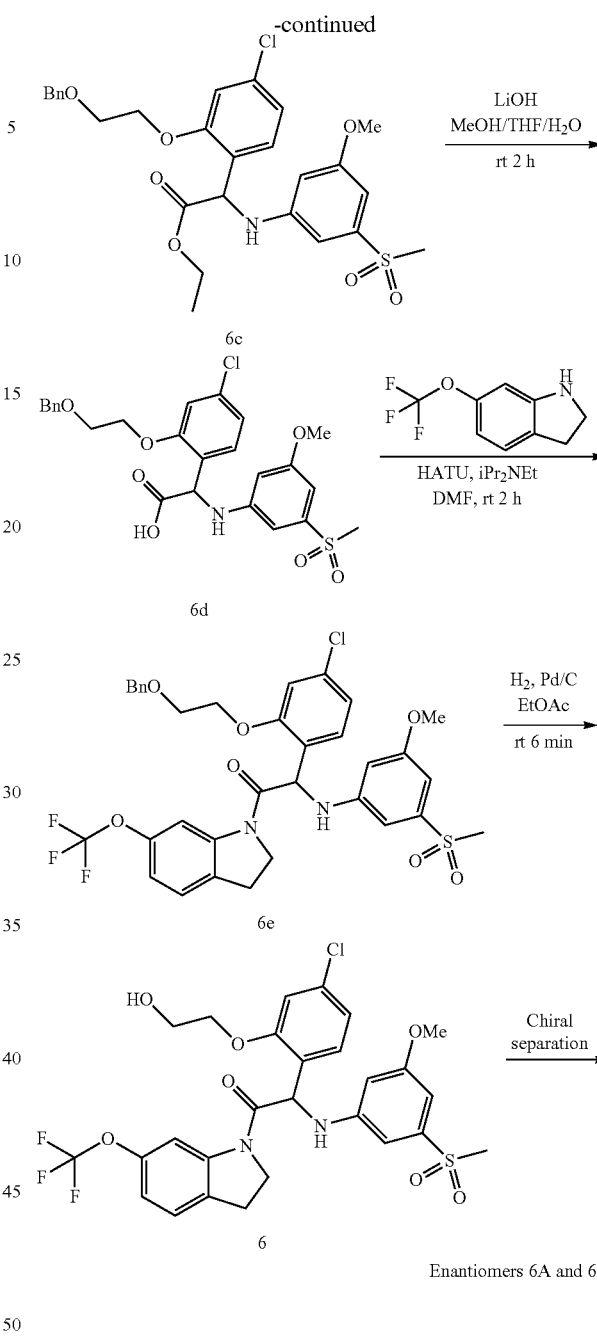

Enantiomers 6A and 6B

Synthesis of Intermediate 6b

To a cooled (−70° C.) solution of 1.5M lithium bis(trimethylsilyl)amide in THF (23 mL, 34.4 mmol) under N$_2$ flow was added a solution of ethyl 2-(2-(2-(benzyloxy)-ethoxy)-4-chlorophenyl)acetate 4a (6 g, 17.2 mmol) in THF (35 mL). After 1 h at −70° C., chlorotrimethylsilane (3.5 mL, 27.5 mmol) was added. The reaction mixture was stirred at −70° C. for 15 min. N-Bromosuccinimide (3.7 g, 20.6 mmol) in THF (35 mL) was added and stirring was continued at −70° C. for 2 h. The reaction mixture was poured into H$_2$O and extracted with EtOAc. The organic phases were combined, dried over MgSO$_4$, filtered and concentrated under reduced pressure to give ethyl 2-(2-(2-(benzyloxy)ethoxy)-4-chlorophenyl)-2-bromoacetate 6b (8.2 g) which was used in the next step without further purification.

Synthesis of Intermediate 6c

A mixture of 2-(2-(2-(benzyloxy)ethoxy)-4-chlorophenyl)-2-bromoacetate 6b (7.36 g, 17.2 mmol), 3-methoxy-5-(methylsulfonyl)aniline [CAS 62606-02-4] (5.2 g, 25.8 mmol) and diisopropylethylamine (5.9 mL, 25.8 mmol) in CH$_3$CN (150 mL) was stirred at 50° C. overnight. The solvent was concentrated under reduced pressure. The residue was diluted with EtOAc and washed with 0.5N HCl and water. The organic layer was dried over MgSO$_4$, filtered and concentrated under reduced pressure. The residue was purified by flash chromatography on silica gel (15-40 µm, 220 g, CH$_2$Cl$_2$/MeOH 99/1). The pure fractions were combined and the solvent was removed under reduced pressure to give ethyl 2-(2-(2-(benzyloxy)ethoxy)-4-chlorophenyl)-2-((3-methoxy-5-(methylsulfonyl)phenyl)amino)acetate 6c (5.52 g).

Synthesis of Intermediate 6d

At 10° C., Lithium hydroxide monohydrate (845 mg, 20.1 mmol) was added to a solution of ethyl 2-(2-(2-(benzyloxy)ethoxy)-4-chlorophenyl)-2-((3-methoxy-5-(methylsulfonyl)phenyl)amino)acetate 6c (5.52 g, 10.1 mmol) in MeOH/THF/water (1/1/1) (90 mL). The mixture was stirred at room temperature for 2 h. The mixture was diluted with ice water and cooled to 0° C. The resulting mixture was acidified to pH 6-7 with 0.5N HCl and extracted with EtOAc. The organic layers were combined, dried over MgSO$_4$, filtered and the solvent was concentrated under reduced pressure to give 2-(2-(2-(benzyloxy)ethoxy)-4-chlorophenyl)-2-((3-methoxy-5-(methylsulfonyl)phenyl)amino)acetic acid 6d (5.26 g). The compound was used in the next reaction step without further purification.

Synthesis of Intermediate 6e

A mixture of 6-(trifluoromethoxy)indoline [CAS 959235-95-1] (1.85 g, 9.12 mmol), 2-(2-(2-(benzyloxy)ethoxy)-4-chlorophenyl)-2-((3-methoxy-5-(methylsulfonyl)phenyl)amino)acetic acid 6d (5.69 g, 10.9 mmol), HATU (5.2 g, 13.7 mmol) and diisopropylethylamine (4.52 mL, 27.4 mmol) in DMF (40 mL) was stirred at room temperature for 2 h. The mixture was diluted with water. The precipitate was filtered off and washed with water. The precipitate was taken up with EtOAc, washed with a 10% solution of K$_2$CO$_3$ in water, water, dried over MgSO$_4$, filtered and the solvent was evaporated under reduced pressure. Purification was performed by flash chromatography on silica gel (15-40 µm, 220 g, heptane/EtOAc 70/30). The pure fractions were combined and concentrated to dryness to give 2-(2-(2-(benzyloxy)ethoxy)-4-chlorophenyl)-2-((3-methoxy-5-(methylsulfonyl)phenyl)amino)-1-(6-(trifluoromethoxy)indolin-1-yl)ethanone 6e (5.6 g).

Synthesis of Compound 6 and Chiral Separation into Enantiomers 6A and 6B

A mixture of 2-(2-(2-(benzyloxy)ethoxy)-4-chlorophenyl)-2-((3-methoxy-5-(methylsulfonyl)phenyl)amino)-1-(6-(trifluoromethoxy)indolin-1-yl)ethanone 6e (5.6 g, 7.94 mmol) in EtOAc (100 mL) was hydrogenated at atmospheric pressure of H$_2$ in the presence of Pd/C (10%) (1.7 g, 1.59 mmol) as a catalyst for 6 min (until the end of the H$_2$ consumption). The reaction was diluted with EtOAc and filtered through a pad of Celite®. The filtrate was concentrated under reduced pressure to give 2-(4-chloro-2-(2-hydroxyethoxy)phenyl)-2-((3-methoxy-5-(methylsulfonyl)phenyl)amino)-1-(6-(trifluoromethoxy)indolin-1-yl)ethanone (Compound 6) as a racemate (4.6 g, crude compound). The Enantiomers of Compound 6 were separated via chiral SFC (Stationary phase: Chiralcel® OJ-H 5 µm 250×20 mm, mobile phase: 80% CO$_2$, 20% MeOH (+0.3% iPrNH$_2$)). The first eluted enantiomer (1.96 g) was further purified via chiral SFC (Stationary phase: Chiralpak® IA 5 µm 250×20 mm, mobile phase: 74% CO$_2$, 26% iPrOH (+0.3% iPrNH$_2$)), to give after precipitation from heptane/diisopropyl ether, Enantiomer 6A (1.527 g). The second eluted enantiomer (2.10 g) was solidified from heptane/diisopropyl ether to give Enantiomer 6B (1.708 g).

Enantiomer 6A:

$^1$H NMR (500 MHz, DMSO-d$_6$) δ ppm 3.08-3.18 (m, 5H) 3.70-3.83 (m, 5H) 4.05-4.19 (m, 3H) 4.43 (td, J=10.32, 6.46 Hz, 1H) 4.97 (t, J=5.52 Hz, 1H) 5.82 (d, J=8.20 Hz, 1H) 6.56 (s, 1H) 6.62 (s, 1H) 6.91 (s, 1H) 7.00-7.08 (m, 3H) 7.16 (d, J=1.58 Hz, 1H) 7.34 (d, J=8.20 Hz, 2H) 8.04 (s, 1H)

LC/MS (method LC-A): R$_t$ 3.32 min, MH$^+$ 615

[α]$_D^{20}$: +64.3° (c 0.305, DMF)

Chiral SFC (method SFC-E): R$_t$ 2.82 min, MH$^+$ 615, chiral purity 100%.

Enantiomer 6B:

$^1$H NMR (500 MHz, DMSO-d$_6$) δ ppm 3.08-3.18 (m, 5H) 3.70-3.83 (m, 5H) 4.05-4.19 (m, 3H) 4.43 (td, J=10.32, 6.46 Hz, 1H) 4.97 (t, J=5.52 Hz, 1H) 5.82 (d, J=8.20 Hz, 1H) 6.56 (s, 1H) 6.62 (s, 1H) 6.91 (s, 1H) 7.00-7.08 (m, 3H) 7.16 (d, J=1.58 Hz, 1H) 7.34 (d, J=8.20 Hz, 2H) 8.04 (s, 1H)

LC/MS (method LC-A): R$_t$ 3.31 min, MH$^+$ 615

[α]$_D^{20}$: −53.7° (c 0.3, DMF)

Chiral SFC (method SFC-E): R$_t$ 3.34 min, MH$^+$ 615, chiral purity 95.7%.

Example 7: Synthesis of 4-(5-chloro-2-(1-((3-methoxy-5-(methylsulfonyl)phenyl)-amino)-2-oxo-2-(6-(trifluoromethyl)indolin-1-yl)ethyl)phenoxy) butanoic acid (Compound 7) and Chiral Separation into Enantiomers 7A and 7B

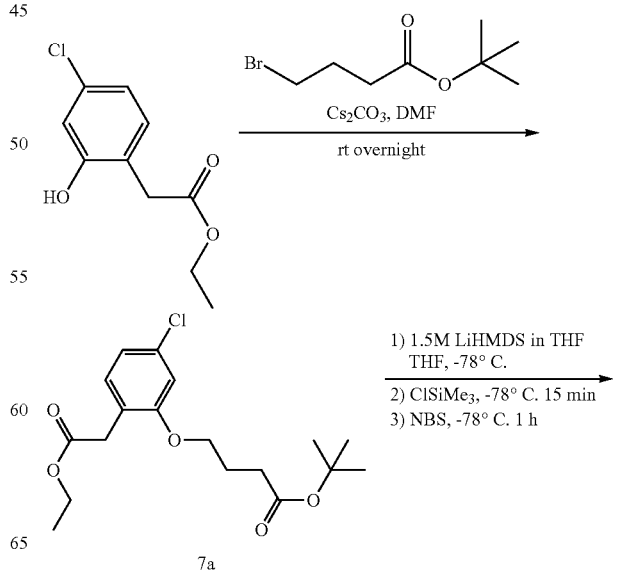

7a

-continued

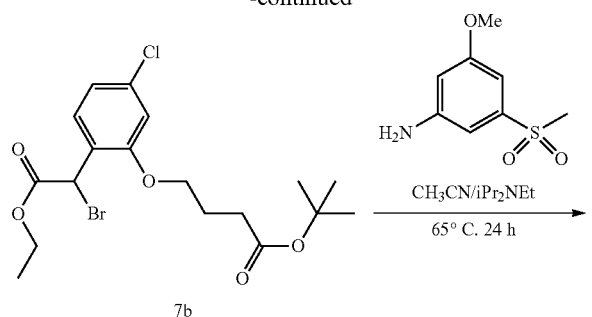

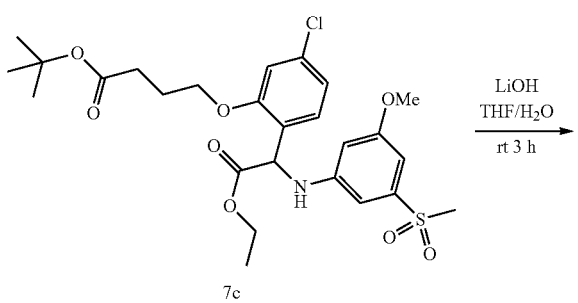

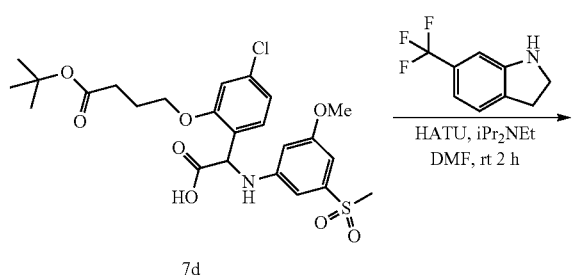

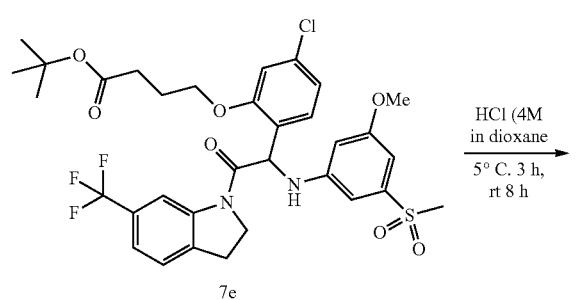

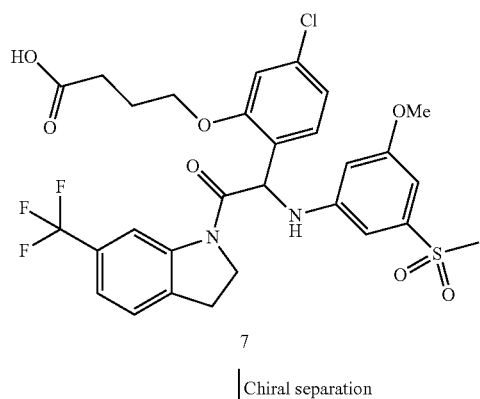

Chiral separation

Enantiomers 7A and 7B

Synthesis of Intermediate 7a

To a suspension of ethyl 2-(4-chloro-2-hydroxyphenyl) acetate [CAS 1261826-30-5] (8.5 g, 39.6 mmol), $Cs_2CO_3$ (25.8 g, 79.2 mmol) in DMF (130 mL) at 10° C. was added dropwise tert-butyl 4-bromobutanoate [CAS 110611-91-1] (7 mL, 39.6 mmol). The mixture was stirred at room temperature overnight. The mixture was diluted with EtOAc and water. The layers were separated. The organic layer was washed with water, dried over $MgSO_4$, filtered and the solvent was concentrated under reduced pressure. Purification was performed by flash chromatography on silica gel (15-40 µm, 120 g, heptane/EtOAc 90/10). The pure fractions were combined and concentrated to dryness to give tert-butyl 4-(5-chloro-2-(2-ethoxy-2-oxoethyl)phenoxy)butanoate 7a (12.7 g).

Synthesis of Intermediate 7b

A flask was charged with LiHMDS 1.5 M in THF (23.5 mL, 35.3 mmol) under $N_2$ flow and was cooled to −78° C. A solution of tert-butyl 4-(5-chloro-2-(2-ethoxy-2-oxoethyl) phenoxy)butanoate 7a (6.3 g, 17.6 mmol) in THF (60 mL) was added dropwise and the mixture was stirred at −78° C. for 15 min. Chlorotrimethylsilane (3.6 mL, 28.3 mmol) was added. After 15 min at −78° C., N-bromosuccinimide (3.77 g, 21.2 mmol) in THF (40 mL) was added and the mixture was stirred at −70° C. for 1 h. The reaction was quenched with water and extracted with EtOAc. The organic layer was washed with water, dried over $MgSO_4$, filtered and the solvent was concentrated under reduced pressure to yield tert-butyl 4-(2-(1-bromo-2-ethoxy-2-oxoethyl)-5-chlorophenoxy)butanoate 7b (7.6 g). The compound was used in the next reaction step without further purification.

Synthesis of Intermediate 7c

To a solution of tert-butyl 4-(2-(1-bromo-2-ethoxy-2-oxoethyl)-5-chlorophenoxy)butanoate 7b (7.6 g, 17.4 mmol) in $CH_3CN$ (140 mL) at room temperature, was added diisopropylethylamine (4.8 mL, 27.9 mmol) and then 3-methoxy-5-(methylsulfonyl)aniline [CAS 62606-02-4] (4.2 g, 20.9 mmol). The mixture was stirred at 65° C. for 24 h. The mixture was diluted with EtOAc, then washed with HCl 0.5 N (twice) and water. The organic layer was dried over $MgSO_4$, filtered and the solvent was concentrated under reduced pressure. Purification was performed by flash chromatography on silica gel (15-40 µm, 120 g, heptane/EtOAc 85/15 to 70/30). The pure fractions were combined and concentrated to dryness to give tert-butyl 4-(5-chloro-2-(2-ethoxy-1-((3-methoxy-5-(methylsulfonyl)phenyl)amino)-2-oxoethyl)phenoxy)butanoate 7c (7.3 g).

Synthesis of Intermediate 7d

Tert-butyl 4-(5-chloro-2-(2-ethoxy-1-((3-methoxy-5-(methylsulfonyl)phenyl)amino)-2-oxoethyl)phenoxy)butanoate 7c (7.3 g, 13.1 mmol) and lithium hydroxide monohydrate (1.65 g, 39.4 mmol) in THF/water (1/1) (180 mL) was stirred at room temperature for 3 h. The mixture was diluted with water. The aqueous layer was slowly acidified with 3N HCl and extracted with EtOAc. The combined organic layers were dried over $MgSO_4$, filtered and the solvent was concentrated under reduced pressure to give 2-(2-(4-(tert-butoxy)-4-oxobutoxy)-4-chlorophenyl)-2-((3- methoxy-5-(methylsulfonyl)phenyl)amino)acetic acid 7d (6.9 g). The product was used in the next reaction step without further purification.

Synthesis of Intermediate 7e

A mixture of 6-(trifluoromethyl)indoline [CAS 181513-29-1] (390 mg, 2.08 mmol), 2-(2-(4-(tert-butoxy)-4-oxobutoxy)-4-chlorophenyl)-2-((3-methoxy-5-(methylsulfonyl)phenyl)amino)acetic acid 7d (1.1 g, 2.08 mmol), HATU (1.2 g, 3.12 mmol) and diisopropylethylamine (1 mL, 6.25 mmol) in DMF (40 mL) was stirred at room temperature for 2 h. The mixture was diluted with water. The precipitate was filtered off and washed with water. The precipitate was taken up with EtOAc, washed with an aqueous solution of $K_2CO_3$ 10%, water, dried over $MgSO_4$, filtered and the solvent was concentrated under reduced pressure. Purification was performed by flash chromatography on silica gel (15-40 μm, 80 g, $CH_2Cl_2$/MeOH 99.5/0.5) to give, after crystallization from $CH_3CN$, tert-butyl 4-(5-chloro-2-(1-((3-methoxy-5-(methylsulfonyl)phenyl)amino)-2-oxo-2-(6-(trifluoromethyl)indolin-1-yl)ethyl)phenoxy)butanoate 7e (700 mg).

Synthesis of Compound 7 and Chiral Separation into Enantiomers 7A and 7B

A solution of tert-butyl 4-(5-chloro-2-(1-((3-methoxy-5-(methylsulfonyl)phenyl)amino)-2-oxo-2-(6-(trifluoromethyl)indolin-1-yl)ethyl)phenoxy)butanoate 7e (0.6 g, 0.143 mmol) in HCl 4M in dioxane (6 ml) was stirred at 5° C. for 3 h and at room temperature for 8 h. The solvent was removed under reduced pressure and the product was crystallized from diisopropyl ether to yield 4-(5-chloro-2-(1-((3-methoxy-5-(methylsulfonyl)phenyl)amino)-2-oxo-2-(6-(trifluoromethyl)indolin-1-yl)ethyl)phenoxy)butanoic acid (Compound 7, 530 mg) as a racemate. The Enantiomers were separated via Preparative Chiral SFC (Stationary phase: Chiralpak® IC 5 μm 250×30 mm, Mobile phase: 65% $CO_2$, 35% MeOH). The first eluted enantiomer (264 mg) was crystallized from $CH_3CN$/diisopropyl ether to give Enantiomer 7A (207 mg). The second eluted enantiomer (269 mg) was crystallized from $CH_3CN$/diisopropyl ether to give Enantiomer 7B (212 mg).

Compound 7:
$^1$H NMR (500 MHz, DMSO-$d_6$) δ ppm 1.90-2.09 (m, 2H) 2.31-2.43 (m, 2H) 3.12 (s, 3H) 3.17-3.28 (m, 2H) 3.74 (s, 3H) 3.88-4.07 (m, 1H) 4.07-4.15 (m, 2H) 4.35-4.45 (m, 1H) 5.73 (br d, J=7.88 Hz, 1H) 6.55 (br s, 1H) 6.64 (br s, 1H) 6.90 (br s, 1H) 7.04 (br s, 2H) 7.16 (br s, 1H) 7.31 (br d, J=7.88 Hz, 1H) 7.39 (br d, J=7.25 Hz, 1H) 7.46 (br d, J=7.25 Hz, 1H) 8.39 (br s, 1H) 12.12 (br s, 1H)
LC-MS (method LC-A): $R_t$ 2.73 min, MH$^+$ 641
Melting point: 210° C.
Enantiomer 7A:
$^1$H NMR (400 MHz, DMSO-$d_6$) δ ppm 1.99 (dq, J=13.26, 6.86 Hz, 2H) 2.30-2.46 (m, 2H) 3.10 (s, 3H) 3.15-3.37 (m, 2H) 3.74 (s, 3H) 3.95-4.06 (m, 1H) 4.07-4.17 (m, 2H) 4.34-4.43 (m, 1H) 5.72 (d, J=8.08 Hz, 1H) 6.54 (s, 1H) 6.63 (s, 1H) 6.89 (s, 1H) 6.99-7.05 (m, 2H) 7.14 (d, J=1.52 Hz, 1H) 7.31 (d, J=8.08 Hz, 1H) 7.38 (d, J=7.58 Hz, 1H) 7.45 (d, J=8.08 Hz, 1H) 8.38 (s, 1H) 12.09 (br s, 1H)
LC/MS (method LC-A): $R_t$ 2.73 min, MH$^+$ 641
[α]$_D^{20}$: −49.8° (c 0.225, DMF)
Chiral SFC (method SFC-F): $R_t$ 3.13 min, no MS response, chiral purity 100%.
Melting point: 182° C.
Enantiomer 7B:
$^1$H NMR (400 MHz, DMSO-$d_6$) δ ppm 1.99 (dq, J=13.26, 6.86 Hz, 2H) 2.30-2.46 (m, 2H) 3.10 (s, 3H) 3.15-3.37 (m, 2H) 3.74 (s, 3H) 3.95-4.06 (m, 1H) 4.07-4.17 (m, 2H) 4.34-4.43 (m, 1H) 5.72 (d, J=8.08 Hz, 1H) 6.54 (s, 1H) 6.63 (s, 1H) 6.89 (s, 1H) 6.99-7.05 (m, 2H) 7.14 (d, J=1.52 Hz, 1H) 7.31 (d, J=8.08 Hz, 1H) 7.38 (d, J=7.58 Hz, 1H) 7.45 (d, J=8.08 Hz, 1H) 8.38 (s, 1H) 12.09 (br s, 1H)
LC/MS (method LC-A): $R_t$ 2.73 min, MH$^+$ 641
[α]$_D^{20}$: +49.3° (c 0.2333, DMF)
Chiral SFC (method SFC-F): $R_t$ 4.34 min, no MS response, chiral purity 100%.
Melting point: 180° C.

Example 8: Synthesis of 4-(5-chloro-2-(1-((3-methoxy-5-(methylsulfonyl)-phenyl)amino)-2-(5-methoxy-6-(trifluoromethyl)indolin-1-yl)-2-oxoethyl)phenoxy)-butanoic acid (Compound 8) and Chiral Separation into Enantiomers 8A and 8B

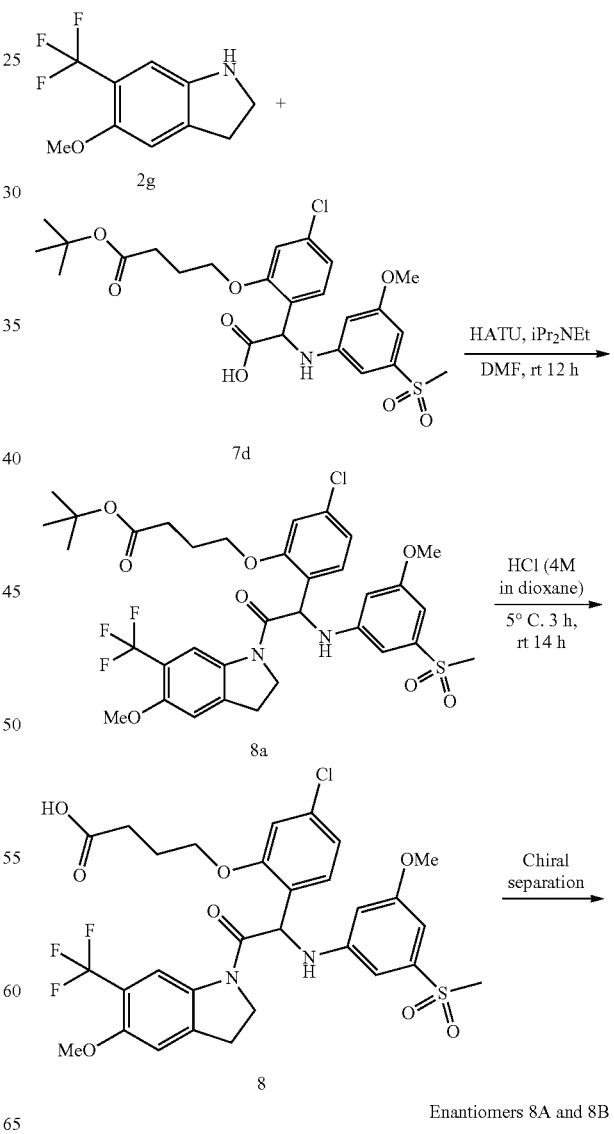

Enantiomers 8A and 8B

Synthesis of Intermediate 8a

A mixture of 5-methoxy-6-(trifluoromethyl)indoline 2g (617 mg, 2.84 mmol), 2-(2-(4-(tert-butoxy)-4-oxobutoxy)-4-chlorophenyl)-2-((3-methoxy-5-(methylsulfonyl)phenyl)amino)acetic acid 7d (1.5 g, 2.84 mmol), HATU (1.62 g, 4.26 mmol) and diisopropylethylamine (1.4 mL, 8.5 mmol) in DMF (60 mL) was stirred at room temperature for 12 h. The mixture was diluted with water. The precipitate was filtered off and washed with water. The precipitate was taken up with EtOAc, washed with an aqueous solution of $K_2CO_3$ 10%, water, dried over $MgSO_4$, filtered and the solvent was concentrated under reduced pressure. Purification was performed by flash chromatography on silica gel (15-40 μm, 120 g, heptane/EtOAc 60/40) to give, after crystallization from petroleum ether/diisopropyl ether, tert-butyl 4-(5-chloro-2-(1-((3-methoxy-5-(methylsulfonyl)phenyl)amino)-2-(5-methoxy-6-(trifluoromethyl)indolin-1-yl)-2-oxoethyl)phenoxy)butanoate 8a (1.36 g).

Synthesis of Compound 8 and Chiral Separation into Enantiomers 8A and 8B

A solution of tert-butyl 4-(5-chloro-2-(1-((3-methoxy-5-(methylsulfonyl)phenyl)amino)-2-(5-methoxy-6-(trifluoromethyl)indolin-1-yl)-2-oxoethyl)phenoxy)butanoate 8a (1.36 g, 1.87 mmol) in HCl 4M in dioxane (12 ml) was stirred at 5° C. for 3 h and at room temperature for 14 h. The precipitate was filtered off and washed with dioxane/diisopropyl ether to yield 4-(5-chloro-2-(1-((3-methoxy-5-(methylsulfonyl)phenyl)amino)-2-(5-methoxy-6-(trifluoromethyl)indolin-1-yl)-2-oxoethyl)phenoxy)butanoic acid (Compound 8, 1.2 g) as a racemate (contaminated with 2.2% of intermediate 8a). A small fraction (40 mg) was further purified via achiral SFC (Stationary phase: 2-ethylpyridine 6 μm 150×21.2 mm, mobile phase: 60% $CO_2$, 40% iPrOH) to yield, after crystallization from $CH_3CN$/diisopropyl ether, 28 mg of compound 8. The remaining amount of Compound 8 was used to separate the enantiomers via Preparative Chiral SFC (Stationary phase: Chiralpak® IC 5 μm 250×30 mm, Mobile phase: 60% $CO_2$, 40% MeOH). The first eluted enantiomer (340 mg) was solidified in petroleum ether/diisopropyl ether to give Enantiomer 8A (285 mg). The second eluted enantiomer (334 mg) was solidified in petroleum ether/diisopropyl ether to give Enantiomer 8B (210 mg).

Compound 8:
$^1$H NMR (400 MHz, DMSO-$d_6$) δ ppm 1.95-2.08 (m, 2H) 2.32-2.44 (m, 2H) 3.08-3.27 (m, 5H) 3.73 (s, 3H) 3.84 (s, 3H) 3.92-4.00 (m, 1H) 4.12 (br d, J=3.54 Hz, 2H) 4.32-4.40 (m, 1H) 5.69 (br d, J=8.08 Hz, 1H) 6.54 (br s, 1H) 6.62 (s, 1H) 6.87 (s, 1H) 6.98-7.04 (m, 2H) 7.14 (s, 1H) 7.22 (s, 1H) 7.31 (d, J=8.08 Hz, 1H) 8.34 (s, 1H) 12.07 (br s, 1H)
LC-MS (method LC-A): $R_t$ 2.74 min, MH$^+$ 671
Melting point: 232° C.

Enantiomer 8A:
$^1$H NMR (500 MHz, DMSO-$d_6$) δ ppm 1.95-2.07 (m, 2H) 2.35-2.47 (m, 2H) 3.11 (s, 3H) 3.15-3.31 (m, 2H) 3.74 (s, 3H) 3.85 (s, 3H) 3.91-4.02 (m, 1H) 4.06-4.19 (m, 2H) 4.37 (td, J=10.25, 6.31 Hz, 1H) 5.70 (d, J=8.20 Hz, 1H) 6.54 (s, 1H) 6.63 (s, 1H) 6.88 (s, 1H) 7.02 (d, J=8.20 Hz, 2H) 7.12-7.17 (m, 1H) 7.23 (s, 1H) 7.31 (d, J=8.20 Hz, 1H) 8.34 (s, 1H) 12.13 (br s, 1H)
LC/MS (method LC-A): $R_t$ 2.75 min, MH$^+$ 671
$[α]_D^{20}$: −52.9° (c 0.28, DMF)
Chiral SFC (method SFC-G): $R_t$ 2.50 min, MH$^+$ 671, chiral purity 100%.

Enantiomer 8B:
$^1$H NMR (500 MHz, DMSO-$d_6$) δ ppm 1.95-2.07 (m, 2H) 2.35-2.47 (m, 2H) 3.11 (s, 3H) 3.15-3.31 (m, 2H) 3.74 (s, 3H) 3.85 (s, 3H) 3.91-4.02 (m, 1H) 4.06-4.19 (m, 2H) 4.37 (td, J=10.25, 6.31 Hz, 1H) 5.70 (d, J=8.20 Hz, 1H) 6.54 (s, 1H) 6.63 (s, 1H) 6.88 (s, 1H) 7.02 (d, J=8.20 Hz, 2H) 7.12-7.17 (m, 1H) 7.23 (s, 1H) 7.31 (d, J=8.20 Hz, 1H) 8.34 (s, 1H) 11.44 (br s, 1H)
LC/MS (method LC-A): $R_t$ 2.73 min, MH$^+$ 671
$[α]_D^{20}$: +46.4° (c 0.28, DMF)
Chiral SFC (method SFC-G): $R_t$ 3.31 min, MH$^+$ 671, chiral purity 100%.

Example 9: Synthesis of 4-(5-chloro-2-(1-((3-methoxy-5-(methylsulfonyl)phenyl)-amino)-2-oxo-2-(6-(trifluoromethoxy)indolin-1-yl)ethyl)phenoxy)butanoic acid (Compound 9) and Chiral Separation into Enantiomers 9A and 9B

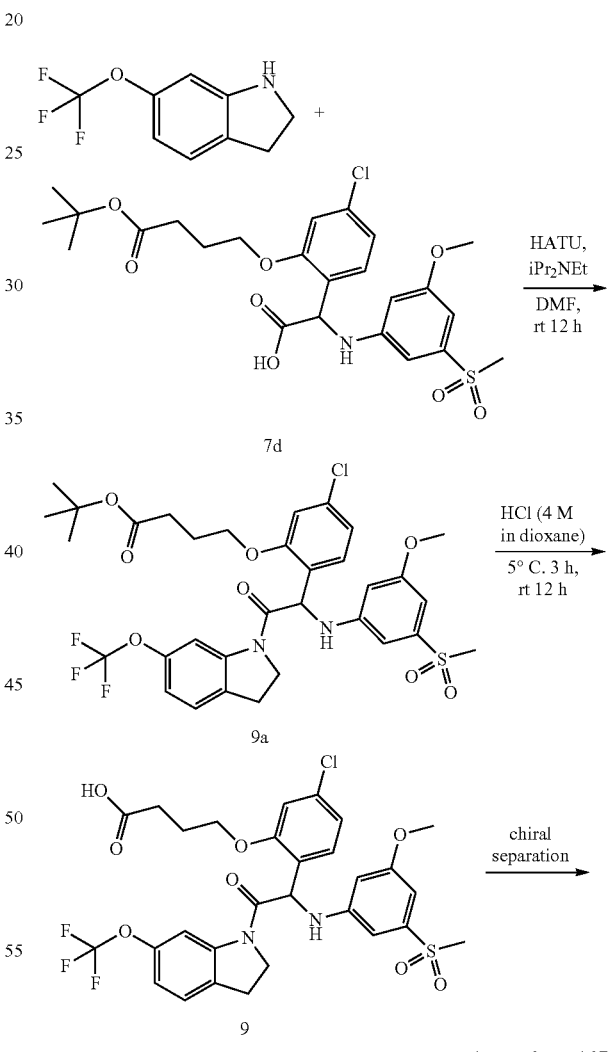

enantiomers 9A and 9B

Synthesis of Intermediate 9a

A mixture of 6-(trifluoromethoxy)indoline [CAS 959235-95-1] (577 mg, 2.84 mmol), 2-(2-(4-(tert-butoxy)-4-oxobutoxy)-4-chlorophenyl)-2-((3-methoxy-5-(methylsulfonyl)

phenyl)amino)acetic acid 7d (1.5 g, 2.84 mmol), HATU (1.62 g, 4.26 mmol) and diisopropylethylamine (1.4 mL, 8.5 mmol) in DMF (60 mL) was stirred at room temperature for 12 h. The mixture was diluted with water. The precipitate was filtered off and washed with water. The precipitate was taken up with EtOAc, washed with an aqueous solution of $K_2CO_3$ 10%, water, dried over $MgSO_4$, filtered and the solvent was concentrated under reduced pressure. Purification was performed by flash chromatography on silica gel (15-40 μm, 120 g, heptane/EtOAc 60/40) to give, after crystallization from petroleum ether/diisopropyl ether, tert-butyl 4-(5-chloro-2-(1-((3-methoxy-5-(methylsulfonyl)phenyl)amino)-2-oxo-2-(6-(trifluoromethoxy)indolin-1-yl)ethyl)phenoxy)butanoate 9a (1.02 g).

Synthesis of Compound 9 and Chiral Separation into Enantiomers 9A and 9B

A solution of tert-butyl 4-(5-chloro-2-(1-((3-methoxy-5-(methylsulfonyl)phenyl)amino)-2-oxo-2-(6-(trifluoromethoxy)indolin-1-yl)ethyl)phenoxy)butanoate 9a (1.02 g, 1.43 mmol) in HCl 4M in dioxane (10 ml) was stirred at 5° C. for 3 h and at room temperature for 12 h. The precipitate was filtered off and washed with dioxane/diisopropyl ether to yield 4-(5-chloro-2-(1-((3-methoxy-5-(methylsulfonyl)phenyl)amino)-2-oxo-2-(6-(trifluoromethoxy)indolin-1-yl)ethyl)phenoxy)butanoic acid (Compound 9, 930 mg, 0.78 equiv. HCl, 0.08 equiv. $H_2O$, 0.162 equiv. dioxane (determined by titration)) as a racemate. The Enantiomers were separated via Preparative Chiral SFC (Stationary phase: Chiralpak® IC 5 μm 250×30 mm, Mobile phase: 70% $CO_2$, 30% EtOH/iPrOH (50/50)). The first eluted enantiomer was stirred up in a mixture of 1N HCl and EtOAc. The organic layer was separated, dried over $MgSO_4$, filtered and the solvent was concentrated under reduced pressure. The compound was crystallized from $CH_3CN$/diisopropyl ether to give Enantiomer 9A (145 mg). The second eluted enantiomer was stirred up in a mixture of 1N HCl and EtOAc. The organic layer was separated, dried over $MgSO_4$, filtered and the solvent was concentrated under reduced pressure. The compound was crystallized from $CH_3CN$/diisopropyl ether to give Enantiomer 9B (156 mg).

Compound 9:
$^1$H NMR (400 MHz, DMSO-$d_6$) δ ppm 1.99 (dq, J=13.71, 7.05 Hz, 2H) 2.32-2.46 (m, 2H) 3.08-3.20 (m, 5H) 3.74 (s, 3H) 4.00 (td, J=10.23, 7.33 Hz, 1H) 4.07-4.15 (m, 2H) 4.38 (td, J=10.23, 6.82 Hz, 1H) 5.70 (s, 1H) 6.54 (s, 1H) 6.63 (s, 1H) 6.88 (s, 1H) 6.95-7.09 (m, 2H) 7.14 (d, J=1.52 Hz, 1H) 7.30 (br d, J=8.08 Hz, 1H) 7.33 (br d, J=8.59 Hz, 1H) 8.03 (s, 1H)
LC-MS (method LC-A): $R_t$ 2.87 min, MH$^+$ 657
Melting point: 173° C.
Enantiomer 9A:
$^1$H NMR (500 MHz, DMSO-$d_6$) δ ppm 1.91-2.06 (m, 2H) 2.32-2.44 (m, 2H) 3.09-3.23 (m, 5H) 3.74 (s, 3H) 3.98-4.16 (m, 3H) 4.39 (td, J=10.17, 6.78 Hz, 1H) 5.71 (d, J=8.20 Hz, 1H) 6.55 (s, 1H) 6.63 (s, 1H) 6.89 (s, 1H) 7.00-7.08 (m, 2H) 7.15 (s, 1H) 7.30 (d, J=8.20 Hz, 1H) 7.34 (d, J=8.20 Hz, 1H) 8.04 (s, 1H) 12.11 (br s, 1H)
LC/MS (method LC-A): $R_t$ 2.86 min, MH$^+$ 657
$[\alpha]_D^{20}$: −56.5° (c 0.255, DMF)
Chiral SFC (method SFC-H): $R_t$ 4.85 min, MH$^+$ 657, chiral purity 100%.
Melting point: 154° C.
Enantiomer 9B:
$^1$H NMR (500 MHz, DMSO-$d_6$) δ ppm 1.91-2.06 (m, 2H) 2.32-2.44 (m, 2H) 3.09-3.23 (m, 5H) 3.74 (s, 3H) 3.98-4.16 (m, 3H) 4.39 (td, J=10.17, 6.78 Hz, 1H) 5.71 (d, J=8.20 Hz, 1H) 6.55 (s, 1H) 6.63 (s, 1H) 6.89 (s, 1H) 7.00-7.08 (m, 2H) 7.15 (s, 1H) 7.30 (d, J=8.20 Hz, 1H) 7.34 (d, J=8.20 Hz, 1H) 8.04 (s, 1H) 12.11 (br s, 1H)
LC/MS (method LC-A): $R_t$ 2.86 min, MH$^+$ 657
$[\alpha]_D^{20}$: +55.3° (c 0.302, DMF)
Chiral SFC (method SFC-H): $R_t$ 6.34 min, MH$^+$ 657, chiral purity 100%.
Melting point: 155° C.

TABLE

| compounds prepared as described above | | |
|---|---|---|
| Compound | Structure | Optical rotation |
| 1 | 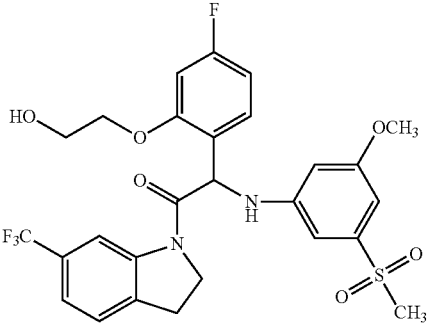 [SMILES: COc1cc(NC(C(=O)N2CCc3ccc(C(F)(F)F)cc32)c2ccc(F)cc2OCCO)cc(S(C)(=O)=O)c1] | racemic |

TABLE-continued compounds prepared as described above

| Compound | Structure | Optical rotation |
| --- | --- | --- |
| 1A | 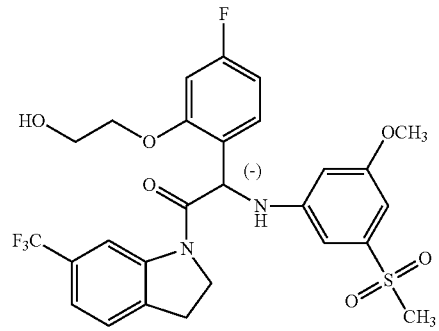 | $[\alpha]_D^{20} = -49.6°$ |
| 1B | 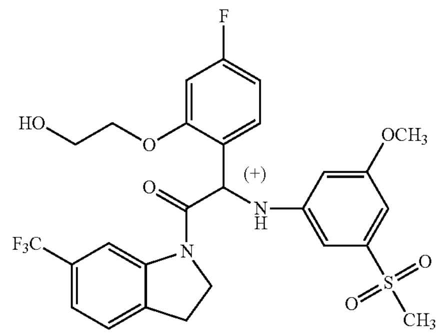 | $[\alpha]_D^{20} = +51.7°$ |
| 2 | 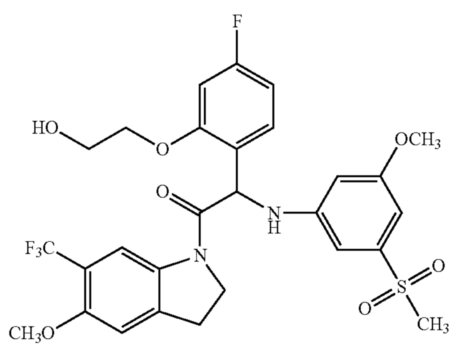 | racemic |
| 2A | 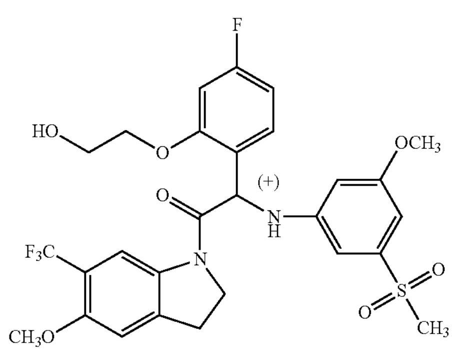 | $[\alpha]_D^{20} = +53.5°$ |

TABLE-continued compounds prepared as described above

| Compound | Structure | Optical rotation |
|---|---|---|
| 2B | (structure) | $[\alpha]_D^{20} = -56.5°$ |
| 3 | (structure) | racemic |
| 3A | (structure) | $[\alpha]_D^{20} = -59.0°$ |
| 3B | (structure) | $[\alpha]_D^{20} = +56.8°$ |

TABLE-continued compounds prepared as described above

| Compound | Structure | Optical rotation |
|---|---|---|
| 4 | [structure] | racemic |
| 4A | [structure with (+)] | $[\alpha]_D^{20} = +59.8°$ |
| 4B | [structure with (−)] | $[\alpha]_D^{20} = -56.4°$ |
| 5 | [structure] | racemic |

TABLE-continued compounds prepared as described above

| Compound | Structure | Optical rotation |
| --- | --- | --- |
| 5A | (structure with 4-chloro-2-(2-hydroxyethoxy)phenyl, (−), 6-trifluoromethyl-5-methoxyindoline, 3-methoxy-5-methylsulfonylphenylamino) | $[\alpha]_D^{20} = -60.4°$ |
| 5B | (structure with 4-chloro-2-(2-hydroxyethoxy)phenyl, (+), 6-trifluoromethyl-5-methoxyindoline, 3-methoxy-5-methylsulfonylphenylamino) | $[\alpha]_D^{20} = +56.7°$ |
| 6 | (structure with 4-chloro-2-(2-hydroxyethoxy)phenyl, 6-trifluoromethoxyindoline, 3-methoxy-5-methylsulfonylphenylamino) | racemic |
| 6A | (structure with 4-chloro-2-(2-hydroxyethoxy)phenyl, (+), 6-trifluoromethoxyindoline, 3-methoxy-5-methylsulfonylphenylamino) | $[\alpha]_D^{20} = +64.3°$ |

TABLE-continued compounds prepared as described above

| Compound | Structure | Optical rotation |
| --- | --- | --- |
| 6B | 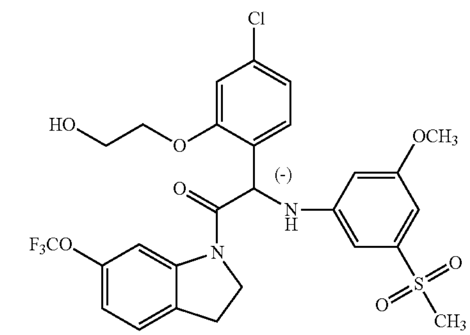 [SMILES: COc1cc(NC(C(=O)N2CCc3ccc(OC(F)(F)F)cc32)c2ccc(Cl)cc2OCCO)cc(S(C)(=O)=O)c1] | $[\alpha]_D^{20} = -53.7°$ |
| 7 | 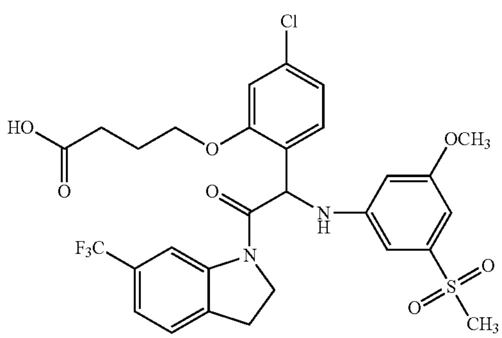 [SMILES: COc1cc(NC(C(=O)N2CCc3ccc(C(F)(F)F)cc32)c2ccc(Cl)cc2OCCCC(=O)O)cc(S(C)(=O)=O)c1] | racemic |
| 7A | 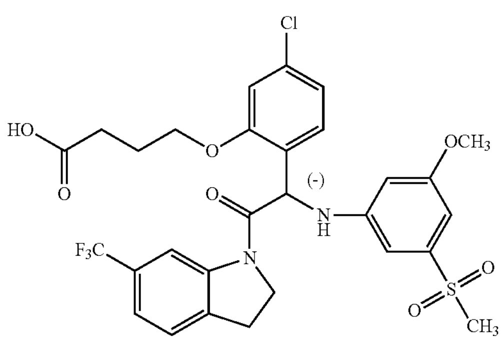 | $[\alpha]_D^{20} = -49.8°$ |
| 7B | 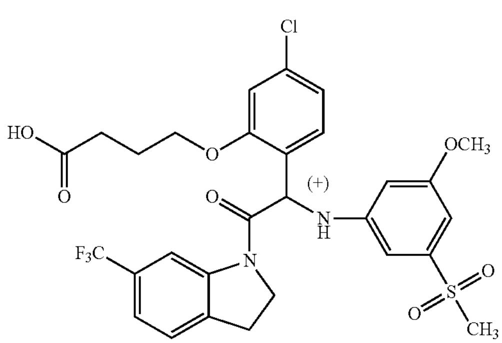 [SMILES: COc1cc(NC(C(=O)N2CCc3ccc(C(F)(F)F)cc32)c2ccc(Cl)cc2OCCCC(=O)O)cc(S(C)(=O)=O)c1] | $[\alpha]_D^{20} = +49.3°$ |

TABLE-continued compounds prepared as described above

| Compound | Structure | Optical rotation |
|---|---|---|
| 8 | 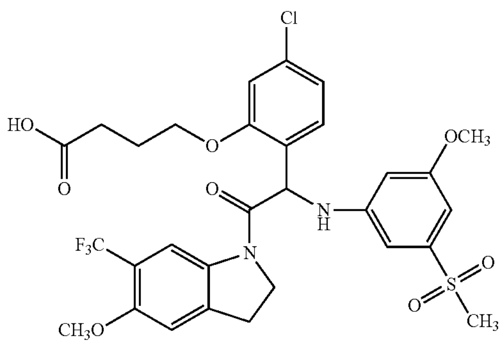 | racemic |
| 8A | 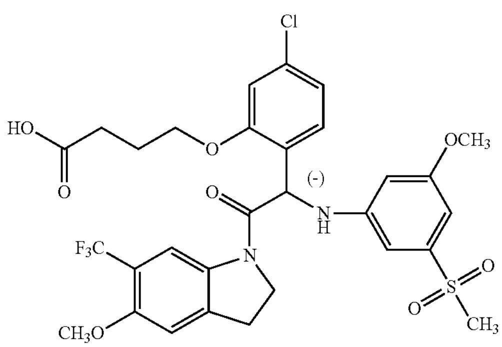 | $[\alpha]_D^{20} = -52.9°$ |
| 8B | 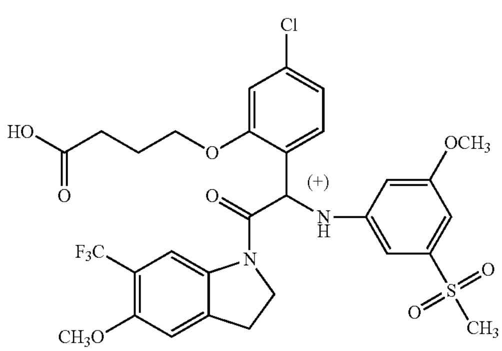 | $[\alpha]_D^{20} = +46.4°$ |
| 9 | 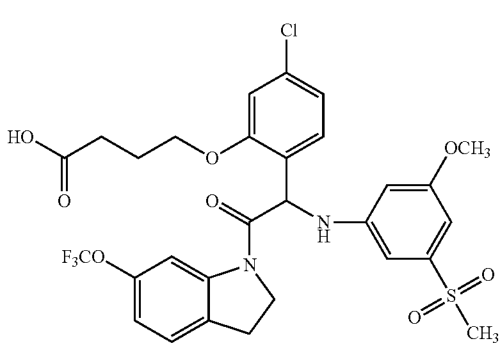 [SMILES: COc1cc(NC(C(=O)N2CCc3ccc(OC(F)(F)F)cc32)c2ccc(Cl)cc2OCCCC(=O)O)cc(S(C)(=O)=O)c1] | racemic |

TABLE-continued compounds prepared as described above

| Compound | Structure | Optical rotation |
|---|---|---|
| 9A | (structure with Cl-substituted phenyl, HO-propyl-O-, F₃CO-indoline, OCH₃-phenyl-sulfonylmethyl, (−) configuration) | $[\alpha]_D^{20} = -56.5°$ |
| 9B | (structure with Cl-substituted phenyl, HO-propyl-O-, F₃CO-indoline, OCH₃-phenyl-sulfonylmethyl, (+) configuration) | $[\alpha]_D^{20} = +55.3°$ |

Antiviral Activity of the Compounds of the Invention
DENV-2 Antiviral Assay

The antiviral activity of all the compounds of the invention was tested against the DENV-2 16681 strain which was labeled with enhanced green fluorescent protein (eGPF). The culture medium consists of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 25 μL was added to 384-well plates (2500 cells/well), which already contain the antiviral compounds. Typically, these plates contain a 5-fold serial dilution of 9 dilution steps of the test compound at 200 times the final concentration in 100% DMSO (200 nL). In addition, each compound concentration is tested in quadruplicate (final concentration range: 25 μM-0.000064 μM or 2.5 μM-0.0000064 μM for the most active compounds). Finally, each plate contains wells which are assigned as virus controls (containing cells and virus in the absence of compound), cell controls (containing cells in the absence of virus and compound) and medium controls (containing medium in the absence of cells, virus and compounds). To the wells assigned as medium control, 25 μL of culture medium was added instead of Vero cells. Once the cells are added to the plates, the plates were incubated for 30 minutes at room temperature to allow the cells to distribute evenly within the wells. Next, the plates were incubated in a fully humidified incubator (37° C., 5% $CO_2$) until the next day. Then, DENV-2 strain 16681, labeled with eGFP, was added at a multiplicity of infection (MOI) of 0.5. Therefore, 15 μL of virus suspension was added to all the wells containing test compound and to the wells assigned as virus control. In parallel, 15 μL of culture medium was added to the medium and cell controls. Next, the plates were incubated for 3 days in a fully humidified incubator (37° C., 5% $CO_2$). At the day of the read out, the eGFP fluorescence was measured using an automated fluorescence microscope at 488 nm (blue laser). Using an in-house LIMS system, inhibition dose response curves for each compound were calculated and the half maximal effective concentration (EC50) was determined. Therefore, the percent inhibition (I) for every test concentration is calculated using the following formula: $I=100*(S_T-S_{CC})/(S_{VC}-S_{CC})$; $S_T$, $S_{CC}$ and $S_{VC}$ are the amount of eGFP signal in the test compound, cell control and virus control wells, respectively. The $EC_{50}$ represents the concentration of a compound at which the virus replication is inhibited with 50%, as measured by a 50% reduction of the eGFP fluorescent intensity compared to the virus control. The $EC_{50}$ is calculated using linear interpolation (Table 1).

In parallel, the toxicity of the compounds was assessed on the same plates. Once the read-out for the eGFP signal was done, 40 μL of ATPlite, a cell viability stain, was added to all wells of the 384-well plates. ATP is present in all metabolically active cells and the concentration declines very rapidly when the cells undergo necrosis or apoptosis. The ATPLite assay system is based on the production of light caused by the reaction of ATP with added luciferase and D-luciferin. The plates were incubated for 10 minutes at room temperature. Next, the plates were measured on a ViewLux. The half maximal cytotoxic concentration ($CC_{50}$) was also determined, defined as the concentration required to reduce the luminescent signal by 50% compared to that of the cell control wells. Finally, the selectivity index (SI) was determined for the compounds, which was calculated as followed: $SI=CC_{50}/EC_{50}$.

TABLE 1

EC$_{50}$, CC$_{50}$, and SI for the compounds of the invention in the DENV-2 antiviral assay

| compound# | EC$_{50}$ (μM) | N | CC$_{50}$ (μM) | N | SI | N |
|---|---|---|---|---|---|---|
| 1 | 0.0032 | 4 | 14 | 4 | 4397 | 4 |
| 1A | 2.4 | 3 | 12 | 3 | 4.8 | 3 |
| 1B | 0.0014 | 3 | 3.4 | 3 | >1980 | 3 |
| 2 | 0.0010 | 4 | 12 | 4 | 13700 | 4 |
| 2A | 0.00093 | 3 | 9.6 | 4 | 16400 | 3 |
| 2B | 0.17 | 3 | 18 | 3 | 105 | 3 |
| 3 | 0.00074 | 3 | 7.9 | 3 | 10700 | 3 |
| 3A | 0.57 | 3 | 11 | 3 | 19 | 3 |
| 3B | 0.00061 | 3 | 8.7 | 3 | 16300 | 3 |
| 4 | 0.00066 | 3 | 7.7 | 3 | 11600 | 3 |
| 4A | 0.00041 | 7 | 6.0 | 7 | 15000 | 7 |
| 4B | 0.016 | 6 | 11 | 7 | 693 | 6 |
| 5 | 0.00070 | 3 | 11 | 3 | 15700 | 3 |
| 5A | 0.076 | 3 | 16 | 3 | 210 | 3 |
| 5B | 0.00023 | 4 | 8.5 | 4 | >16800 | 4 |
| 6 | 0.00043 | 4 | 3.6 | 4 | 7070 | 4 |
| 6A | 0.00023 | 7 | 7.3 | 8 | >12000 | 7 |
| 6B | 0.020 | 5 | 10 | 6 | 492 | 5 |
| 7 | 0.00058 | 3 | 13 | 3 | 21800 | 3 |
| 7A | 0.069 | 3 | 11 | 4 | 165 | 3 |
| 7B | 0.00025 | 5 | 11 | 7 | 90600 | 5 |
| 8 | 0.0019 | 3 | 14 | 3 | 7460 | 3 |
| 8A | 0.095 | 4 | 12 | 5 | 126 | 4 |
| 8B | 0.0012 | 3 | 14 | 3 | 6780 | 3 |
| 9 | 0.00031 | 3 | 12 | 3 | 40200 | 3 |
| 9A | 0.12 | 3 | 12 | 3 | 93 | 3 |
| 9B | 0.00015 | 4 | 13 | 4 | 83000 | 4 |

N = the number of independent experiments in which the compounds were tested.

Tetravalent Reverse Transcriptase Quantitative-PCR (RT-qPCR) Assay

The antiviral activity of the compounds of the invention was tested against DENV-1 strain TC974#666 (NCPV), DENV-2 strain 16681, DENV-3 strain H87 (NCPV) and DENV-4 strain H241 (NCPV) in a RT-qPCR assay. Therefore, Vero cells were infected with either DENV-1, or -2, or -3, or -4 in the presence or absence of test compounds. At day 3 post-infection, the cells were lysed and cell lysates were used to prepare cDNA of both a viral target (the 3'UTR of DENV; Table 2) and a cellular reference gene (1-actin, Table 2). Subsequently, a duplex real time PCR was performed on a Lightcycler480 instrument. The generated Cp value is inversely proportional to the amount of RNA expression of these targets. Inhibition of DENV replication by a test compound results in a shift of Cp's for the 3'UTR gene. On the other hand, if a test compound is toxic to the cells, a similar effect on β-actin expression will be observed. The comparative ΔΔCp method is used to calculate EC$_{50}$, which is based on the relative gene expression of the target gene (3'UTR) normalized with the cellular housekeeping gene (β-actin). In addition, CC$_{50}$ values are determined based on the C$_p$ values acquired for the housekeeping gene β-actin.

TABLE 2

Primers and probes used for the real-time, quantitative RT-PCR.

| Primer/ probe | Target | Sequence[a, b] |
|---|---|---|
| F3utr258 | DENV 3' UTR | 5'-CGGTTAGAGGAGACCCCTC-3' |
| R3utr425 | DENV 3' UTR | 5'-GAGACAGCAGGATCTCTGGTC-3' |
| P3utr343 | DENV 3' UTR | *FAM*-5'-AAGGACTAG-*ZEN*-AGGTTAGAGGAGACCCCCC-3'-/*IABkFQ* |
| Factin743 | β-actin | 5'-GGCCAGGTCATCACCATT-3' |
| Ractin876 | β-actin | 5'-ATGTCCACGTCACACTTCATG-3' |
| Pactin773 | β-actin | *HEX*-5'-TTCCGCTGC-*ZEN*-CCTGAGG CTCTC-3'-*IABkFQ* |

[a]Reporter dyes (FAM, HEX) and quenchers (ZEN and IABkFQ) elements are indicated in bold and italics.
[b]The nucleotide sequence of the primers and probes were selected from the conserved region in the 3'UTR region of the dengue virus genome, based on the alignment of 300 nucleotide sequences of the four dengue serotypes deposited in Genbank (Gong et al., 2013, Methods Mol Biol, Chapter 16).

The culture medium consisted of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 75 μL/well was added in 96-well plates (10000 cells/well), which already contain the antiviral compounds. Typically, these plates contain a 5-fold serial dilution of 9 dilution steps of the test compound at 200 times the final concentration in 100% DMSO (500 nL; final concentration range: 25 μM-0.000064 μM or 2.5 μM-0.0000064 μM for the most active compounds). In addition, each plate contains wells which are assigned as virus controls (containing cells and virus in the absence of compound) and cell controls (containing cells in the absence of virus and compound). Once the cells were added in the plates, the plates were incubated in a fully humidified incubator (37° C., 5% CO$_2$) until the next day. Dengue viruses serotype-1, 2, 3 and 4 were diluted in order to obtain a Cp of ~22-24 in the assay. Therefore, 25 μL of virus suspension was added to all the wells containing test compound and to the wells assigned as virus control. In parallel, 25 μL of culture medium was added to the cell controls. Next, the plates were incubated for 3 days in a fully humidified incubator (37° C., 5% CO$_2$). After 3 days, the supernatant was removed from the wells and the cells were washed twice with ice-cold PBS (~100 μL). The cell pellets within the 96-well plates were stored at −80° C. for at least 1 day. Next, RNA was extracted using the Cells-to-CT™ lysis kit, according to the manufacturer's guideline (Life Technologies). The cell lysates can be stored at −80° C. or immediately used in the reverse transcription step.

In preparation of the reverse transcription step, mix A (table 3A) was prepared and 7.57 μL/well was dispensed in a 96-well plate. After addition of 5 μL of the cell lysates, a five minute denaturation step at 75° C. was performed (table 3B). Afterwards, 7.43 μL of mix B was added (table 3C) and the reverse transcription step was initiated (table 3D) to generate cDNA.

Finally, a RT-qPCR mix was prepared, mix C (table 4A), and 22.02 μL/well was dispensed in 96-well LightCycler qPCR plates to which 3 μL of cDNA was added and the qPCR was performed according to the conditions in table 4B on a LightCycler 480.

Using the LightCycler software and an in-house LIMS system, dose response curves for each compound were calculated and the half maximal effective concentration (EC50) and the half maximal cytotoxic concentration ($CC_{50}$) were determined (Tables 5-8).

TABLE 3 cDNA synthesis using Mix A, denaturation, Mix B and reverse transcription.

A
Mix A

| | | | | | |
|---|---|---|---|---|---|
| Plates | 8 | | | | |
| Samples | 828 | | Reaction Vol. (μl) | 20 | |
| | | Concentration | Volume for (μl) | | |
| Mix Item | Unit | Stock | Final | 1 sample | x samples |
| Milli-Q $H_2O$ | | | | 7.27 | 6019.56 |
| R3utr425 | μM | 20 | 0.27 | 0.15 | 12420 |
| Ractin876 | μM | 20 | 0.27 | 0.15 | 124.20 |
| | | Volume mix/well (μl) | | 7.57 | |
| | | Cell lysates | | 5.00 | |

B
Denaturation step:

| Step | Temp | Time |
|---|---|---|
| Denaturation | 75° C. | 5' |
| Hold | 4° C. | hold |

C
Mix B

| | | | | | |
|---|---|---|---|---|---|
| Samples | 864 | | | | |
| | | Concentration | Volume for (μl) | | |
| Mix Item | Unit | Stock | Final | 1 sample | x samples |
| Expand HIFI buffer 2 | X | 10.00 | 1.00 | 2.00 | 1728.0 |
| $MgCl_2$ | mM | 25.00 | 3.50 | 2.80 | 2419.2 |
| dNTPs | mM | 10.00 | 1.00 | 2.00 | 1728.0 |
| Rnase inhibitor | U/μl | 40.00 | 1.00 | 0.50 | 432.0 |
| Expand RT | U/μl | 50.00 | 0.33 | 0.13 | 112.3 |
| | | Total Volume | | 7.43 | |
| | | Mix (μl) | | | |

D
Protocol cDNA synthesis

| Step | Temp | Time |
|---|---|---|
| Rev transc | 42° C. | 30' |
| Denaturation | 99° C. | 5' |
| Hold | 4° C. | hold |

TABLE 4 qPCR mix and protocol.

A
Mix c

| | | | | | |
|---|---|---|---|---|---|
| Samples | 833 | | Reaction Vol. (μl) | 25 | |
| | | Concentration | Volume for (μl) | | |
| Mix Item | Unit | Stock | Final | 1 sample | x samples |
| $H_2O$ PCR grade Roche | | | | 7.74 | 6447.42 |
| Roche 2xMM mix | X | 2 | 1 | 12.50 | 10412.50 |
| F3utr258 | μM | 20 | 0.3 | 0.38 | 316.54 |
| R3utr425 | μM | 20 | 0.3 | 0.38 | 316.54 |
| P3utr343 | μM | 20 | 0.1 | 0.13 | 108.29 |

TABLE 4-continued qPCR mix and protocol.

| | | | | | |
|---|---|---|---|---|---|
| Factin743 | μM | 20 | 0.3 | 0.38 | 316.54 |
| Ractin876 | μM | 20 | 0.3 | 0.38 | 316.54 |
| Pactin773 | μM | 20 | 0.1 | 0.13 | 108.29 |
| | | Volume Mix/Tube (μl) | | 22.02 | |
| | | cDNA | | 3.00 | |

B
Protocol qPCR3

| Step | Temp | Time | Ramp rate | |
|---|---|---|---|---|
| preincub/denat | 95° C. | 10 min | 4.4 | |
| Denaturation | 95° C. | 10 sec | 4.4 | 40 cycles |
| annealing | 58° C. | 1 min | 2.2 | |
| Elongation | 72° C. | 1 sec | 4.4 | |
| Cooling | 40° C. | 10 sec | 1.5 | |

TABLE 5

$EC_{50}$, $CC_{50}$, and SI for the compounds against serotype 1 in the RT-qPCR assays

| | RT-qPCR serotype 1 TC974#666 | | | | | |
|---|---|---|---|---|---|---|
| compound# | $EC_{50}$ (μM) | N | $CC_{50}$ (μM) | N | SI | N |
| 1B | 0.0015 | 3 | >2.5 | 3 | >2860 | 3 |
| 2A | 0.0046 | 5 | >2.5 | 4 | >981 | 4 |
| 3B | 0.0011 | 3 | >2.5 | 3 | >3640 | 3 |
| 4A | 0.00075 | 3 | >2.5 | 3 | >5470 | 3 |
| 5B | 0.00094 | 4 | 5.1 | 4 | 8640 | 4 |
| 6A | 0.00016 | 3 | >2.5 | 3 | >41300 | 3 |
| 7B | 0.00013 | 3 | >2.5 | 3 | >19200 | 3 |
| 8B | 0.0012 | 3 | 14 | 3 | 10500 | 3 |
| 9B | 0.00010 | 3 | >2.5 | 3 | >45500 | 3 |

N = the number of independent experiments in which the compounds were tested.

TABLE 6

$EC_{50}$, $CC_{50}$, and SI for the compounds against serotype 2 in the RT-qPCR assays

| | RT-qPCR serotype 2 16681 | | | | | |
|---|---|---|---|---|---|---|
| compound# | $EC_{50}$ (μM) | N | $CC_{50}$ (μM) | N | SI | N |
| 1B | 0.0011 | 3 | 4.1 | 3 | 4670 | 3 |
| 2A | 0.0013 | 4 | 12 | 4 | 4910 | 4 |
| 3B | 0.00090 | 3 | 3.6 | 3 | 4760 | 3 |
| 4A | 0.00045 | 3 | 2.7 | 3 | 11700 | 3 |
| 5B | 0.00024 | 5 | 4.2 | 5 | >17100 | 5 |
| 6A | 0.00016 | 3 | 4.2 | 3 | >12600 | 3 |
| 7B | 0.00019 | 3 | >2.5 | 2 | >13500 | 2 |
| 8B | 0.00030 | 3 | 16 | 2 | 54300 | 2 |
| 9B | 0.000068 | 3 | >2.5 | 3 | >56500 | 3 |

N = the number of independent experiments in which the compounds were tested.

TABLE 7

EC$_{50}$, CC$_{50}$, and SI for the compounds against serotype 3 in the RT-qPCR assays

| | RT-qPCR serotype 3 H87 | | | | | |
|---|---|---|---|---|---|---|
| compound# | EC$_{50}$ (µM) | N | CC$_{50}$ (µM) | N | SI | N |
| 1B | 0.020 | 3 | >2.5 | 3 | >127 | 3 |
| 2A | 0.020 | 3 | >2.5 | 3 | >157 | 3 |
| 3B | 0.013 | 3 | >2.5 | 3 | >444 | 3 |
| 4A | 0.013 | 3 | >2.5 | 3 | >234 | 3 |
| 5B | 0.0067 | 4 | >2.5 | 4 | >752 | 4 |
| 6A | 0.0026 | 3 | >2.5 | 3 | >1480 | 3 |
| 7B | 0.0052 | 3 | >2.5 | 3 | >473 | 3 |
| 8B | 0.019 | 3 | 12 | 3 | 796 | 3 |
| 9B | 0.0017 | 3 | >2.5 | 3 | >1840 | 3 |

N = the number of independent experiments in which the compounds were tested.

TABLE 8

EC$_{50}$, CC$_{50}$, and SI for the compounds against serotype 4 in the RT-qPCR assays

| | RT-qPCR serotype 4 H241 | | | | | |
|---|---|---|---|---|---|---|
| compound# | EC$_{50}$ (µM) | N | CC$_{50}$ (µM) | N | SI | N |
| 1B | 0.13 | 3 | >2.4 | 3 | 23 | 3 |
| 2A | 0.10 | 3 | 2.8 | 3 | 35 | 3 |
| 3B | 0.072 | 3 | >2.3 | 3 | >32 | 3 |
| 4A | 0.044 | 4 | 2.2 | 4 | 69 | 4 |
| 5B | 0.026 | 4 | 2.5 | 4 | 86 | 2 |
| 6A | 0.026 | 4 | 2.3 | 4 | 119 | 4 |
| 7B | 0.024 | 3 | >2.5 | 3 | >186 | 3 |
| 8B | 0.084 | 3 | 7.4 | 3 | 88 | 3 |
| 9B | 0.0072 | 3 | 5.0 | 2 | 1390 | 2 |

N = the number of independent experiments in which the compounds were tested.

---

The invention claimed is:

1. A compound of formula (I), including any stereochemically isomeric form thereof,

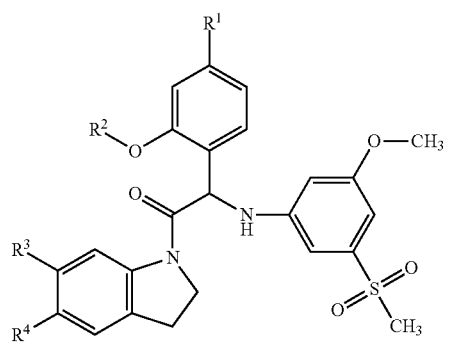

wherein
$R^1$ is fluoro, $R^2$ is —CH$_2$CH$_2$OH, $R^3$ is trifluoromethyl, and $R^4$ is hydrogen, or
$R^1$ is fluoro, $R^2$ is —CH$_2$CH$_2$OH, $R^3$ is trifluoromethyl, and $R^4$ is methoxy, or
$R^1$ is fluoro, $R^2$ is —CH$_2$CH$_2$OH, $R^3$ is trifluoromethoxy, and $R^4$ is hydrogen, or
$R^1$ is chloro, $R^2$ is —CH$_2$CH$_2$OH, $R^3$ is trifluoromethyl, and $R^4$ is hydrogen, or
$R^1$ is chloro, $R^2$ is —CH$_2$CH$_2$OH, $R^3$ is trifluoromethyl, and $R^4$ is methoxy, or
$R^1$ is chloro, $R^2$ is —CH$_2$CH$_2$OH, $R^3$ is trifluoromethoxy, and $R^4$ is hydrogen, or
$R^1$ is chloro, $R^2$ is —(CH$_2$)$_3$COOH, $R^3$ is trifluoromethyl, and $R^4$ is hydrogen, or
$R^1$ is chloro, $R^2$ is —(CH$_2$)$_3$COOH, $R^3$ is trifluoromethyl, and $R^4$ is methoxy, or
$R^1$ is chloro, $R^2$ is —(CH$_2$)$_3$COOH, $R^3$ is trifluoromethoxy, and $R^4$ is hydrogen;
or a pharmaceutically acceptable salt, solvate or polymorph thereof.

2. The compound according to claim 1 wherein said compound is selected from the group consisting of:

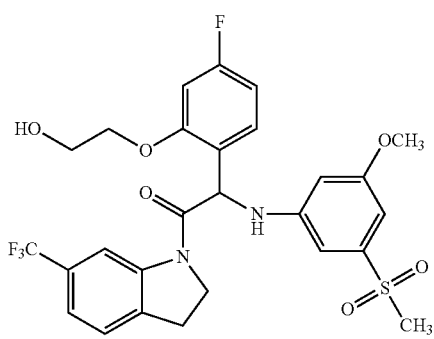

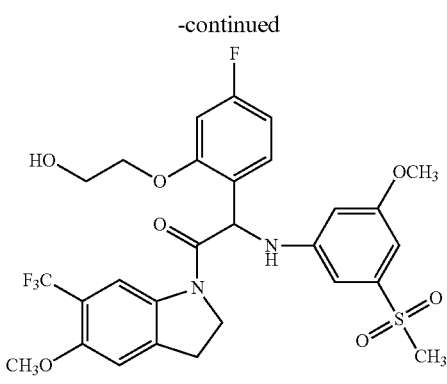

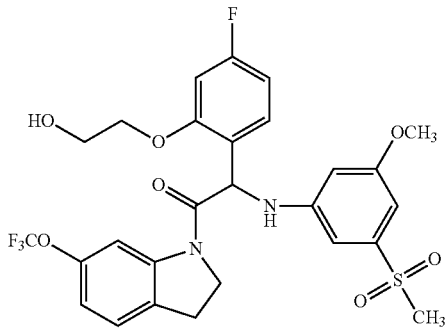

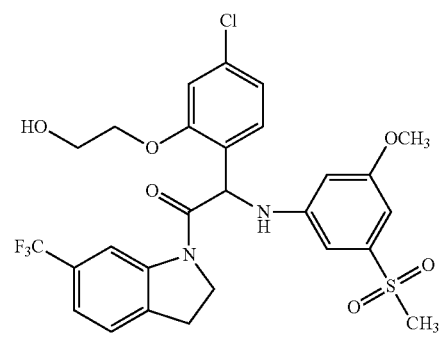

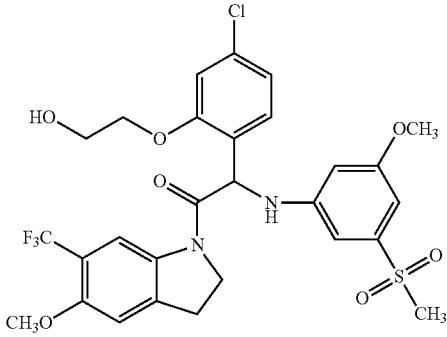

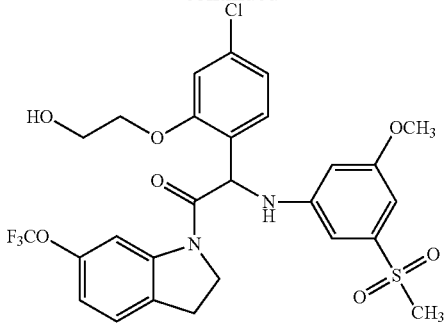
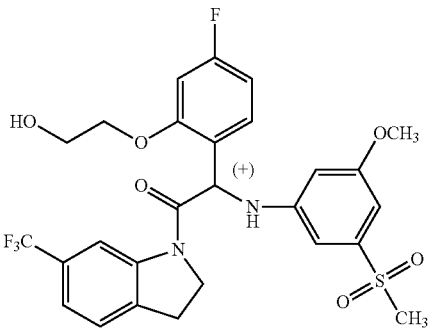
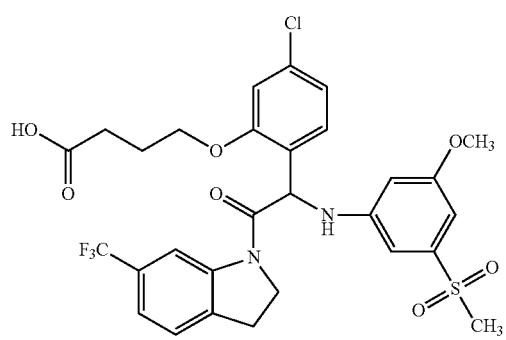
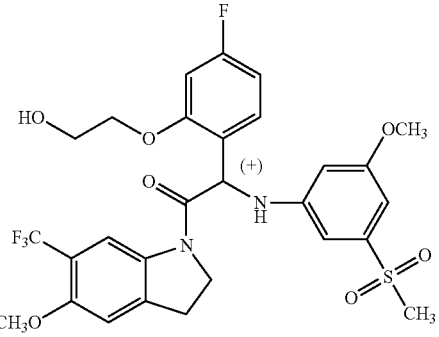
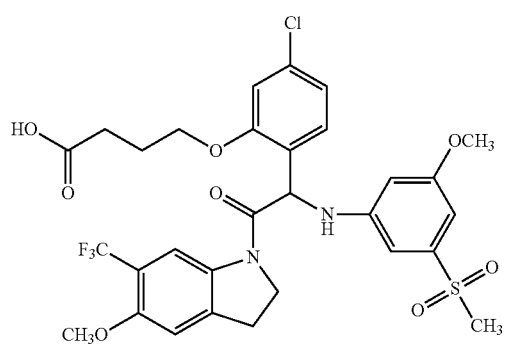
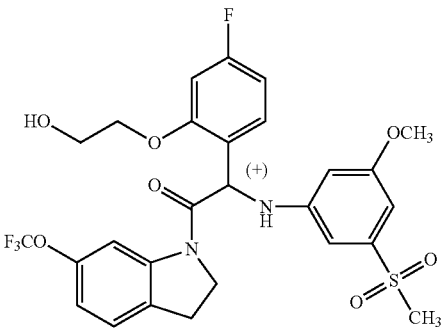
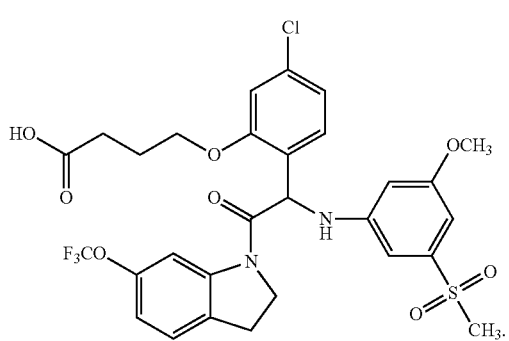 [SMILES: COc1cc(NC(C(=O)N2CCc3ccc(OC(F)(F)F)cc32)c2ccc(Cl)cc2OCCCC(=O)O)cc(S(C)(=O)=O)c1]
and
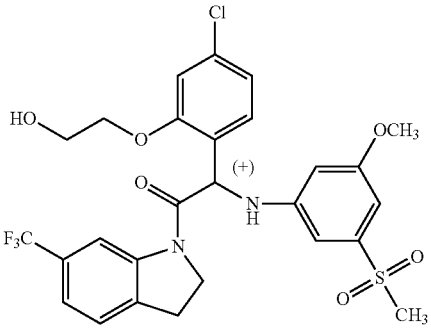
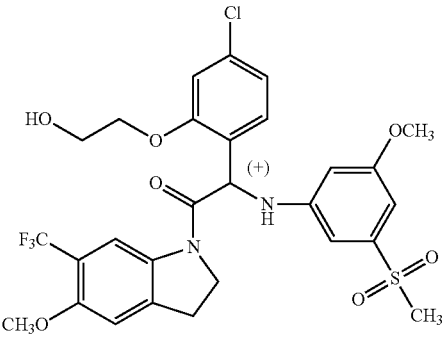
3. The compound according to claim 1 wherein said compound has the (+) specific rotation.
4. The compound according to claim 1 wherein said compound is selected from the group consisting of:

-continued

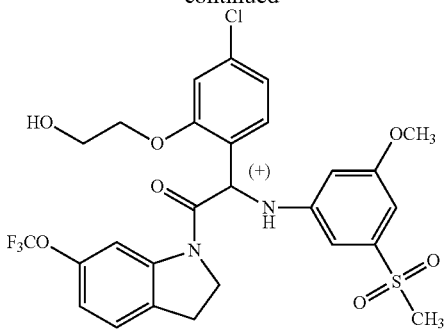

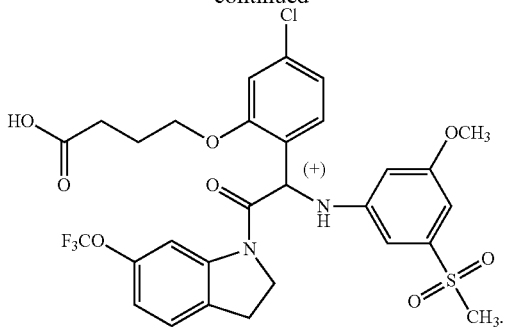

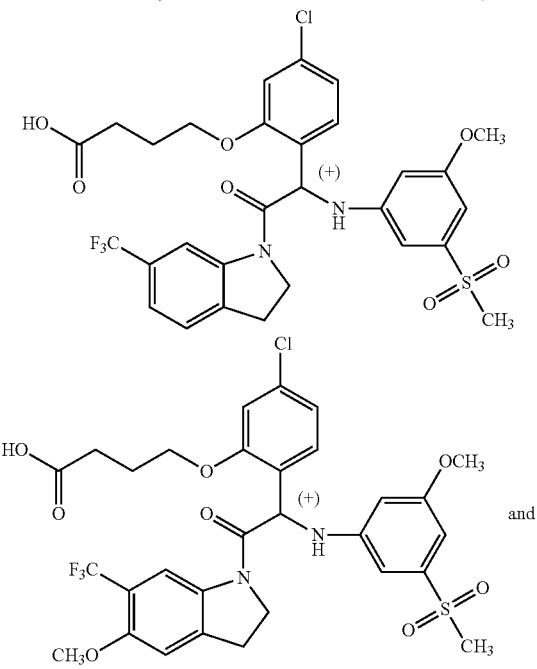

and

5. A pharmaceutical composition comprising the compound according to claim 1 together with one or more pharmaceutically acceptable excipients, diluents or carriers.

6. The pharmaceutical composition according to claim 5 which comprises a second or further active ingredient.

7. The pharmaceutical composition according to claim 6 wherein the second or further active ingredient is an antiviral agent.

8. A method of treating Dengue infection or a disease associated with Dengue infection, comprising administering to a subject in need thereof an effective amount of the compound according to claim 1.

9. The method according to claim 8 wherein the Dengue infection is infection by viruses of the DENV-1, DENV-2, DENV-3 or DENV-4 strain.

10. A method of inhibiting Dengue virus replication in an animal cell, comprising administering to a subject in need thereof an effective amount of the compound according to claim 1.

* * * * *